(12) United States Patent
Deransart et al.

(10) Patent No.: US 10,973,645 B2
(45) Date of Patent: Apr. 13, 2021

(54) SYSTEMS FOR REVERSE SHOULDER IMPLANTS

(71) Applicant: Tornier Orthopedics Ireland, Ltd., County Cork (IE)

(72) Inventors: Pierric Deransart, Saint Martin d'uriage (FR); Vincent Gaborit, Saint Martin d'Hères (FR); Brian Maroney, Fort Wayne, IN (US); Brian C. Hodorek, Winona Lake, IN (US); Shawn M. Gargac, Winona Lake, IN (US); Pascal Boileau, Nice (FR); Gilles Walch, Lyons (FR); Luc Favard, Montlouis (FR); Philippe Clavert, Illkirch Graffenstaden (FR); François Sirveaux, Villers les Nancy (FR); James Kelly, San Francisco, CA (US); Sumant Krishnan, Dallas, TX (US); Daniel Mole, Nancy (FR); Cédric Comte, Biviers (FR); Eric Rundstadler, Echirolles (FR); François Mondi, Domène (FR); Christopher R. Chuinard, Traverse City, MI (US); Thomas Bradley Edwards, Houston, TX (US)

(73) Assignee: Tornier Orthopedics Ireland, Ltd., Cork (IE)

( * ) Notice: Subject to any disclaimer, the term of this patent is extended or adjusted under 35 U.S.C. 154(b) by 0 days.

(21) Appl. No.: 16/020,873

(22) Filed: Jun. 27, 2018

(65) Prior Publication Data

US 2018/0325687 A1 Nov. 15, 2018

Related U.S. Application Data

(63) Continuation of application No. 14/432,463, filed as application No. PCT/EP2013/072634 on Oct. 29, 2013, now Pat. No. 10,034,759.

(Continued)

(51) Int. Cl.
*A61F 2/40* (2006.01)
*A61B 17/56* (2006.01)
*A61F 2/30* (2006.01)

(52) U.S. Cl.
CPC ............ *A61F 2/4014* (2013.01); *A61B 17/56* (2013.01); *A61F 2002/3083* (2013.01);
(Continued)

(58) Field of Classification Search
CPC .............................................. A61F 2/40–4081
See application file for complete search history.

(56) References Cited

U.S. PATENT DOCUMENTS 4,310,931 A   1/1982   Muller
5,108,451 A   4/1992   Forte
(Continued)

FOREIGN PATENT DOCUMENTS

DE        102 50 390      5/2004
DE    10 2005 003 097     7/2006
(Continued)

OTHER PUBLICATIONS

International Search Report and Written Opinion for PCT/EP2013/072634 dated Apr. 7, 2014 in 18 pages.
(Continued)

*Primary Examiner* — Marcia L Watkins
(74) *Attorney, Agent, or Firm* — Duane Morris LLP

(57) ABSTRACT

Embodiments of the present invention include a convertible prosthesis that is capable of conversion from a humeral head replacement to a reverse reconstruction without any removal of parts integrated into the patient's bony anatomy (e.g. implant stems). A desired overall implant inclination angle may be achieved by matching various implant stems with various reverse inserts, thus permitting a resection surface to be matched with an implant stem selection while also
(Continued)

permitting a desired overall implant inclination angle to be achieved through the selection of an appropriate insert.

21 Claims, 25 Drawing Sheets

Related U.S. Application Data

(60) Provisional application No. 61/719,835, filed on Oct. 29, 2012.

(52) U.S. Cl.
CPC ............... *A61F 2002/30332* (2013.01); *A61F 2002/30354* (2013.01); *A61F 2002/30367* (2013.01); *A61F 2002/30485* (2013.01); *A61F 2002/30495* (2013.01); *A61F 2002/30505* (2013.01); *A61F 2002/30604* (2013.01); *A61F 2002/30616* (2013.01); *A61F 2002/4022* (2013.01)

(56) References Cited

U.S. PATENT DOCUMENTS

| | | | |
|---|---|---|---|
| 5,910,171 A | 6/1999 | Kummer et al. | |
| 6,165,224 A | 12/2000 | Tornier | |
| 6,187,012 B1 | 2/2001 | Masini | |
| 6,197,062 B1 | 3/2001 | Fenlin | |
| 6,228,119 B1 | 5/2001 | Ondrla et al. | |
| 6,283,999 B1 | 9/2001 | Rockwood, Jr. | |
| 6,334,874 B1 | 1/2002 | Tornier et al. | |
| 6,398,812 B1 | 6/2002 | Masini | |
| 6,436,147 B1 | 8/2002 | Zweymuller | |
| 6,520,994 B2 | 2/2003 | Nogarin | |
| 6,558,425 B2 | 5/2003 | Rockwood, Jr. | |
| 6,648,894 B2 | 11/2003 | Abdelgany et al. | |
| 6,673,114 B2 | 1/2004 | Hartdegen et al. | |
| 6,702,854 B1 | 3/2004 | Cheal et al. | |
| 6,719,799 B1 | 4/2004 | Kropf | |
| 6,746,487 B2 | 6/2004 | Scifert et al. | |
| 6,887,277 B2 | 5/2005 | Rauscher et al. | |
| 6,899,736 B1 | 5/2005 | Rauscher et al. | |
| 6,942,699 B2 | 9/2005 | Stone et al. | |
| 7,001,389 B1* | 2/2006 | Navarro ............ A61B 17/8047 | 606/281 |
| 7,011,686 B2* | 3/2006 | Ball ................... A61F 2/4014 | 623/19.14 |
| 7,166,132 B2 | 1/2007 | Callaway et al. | |
| 7,175,663 B1 | 2/2007 | Stone | |
| 7,309,360 B2 | 12/2007 | Tornier et al. | |
| 7,445,638 B2 | 11/2008 | Benguin et al. | |
| 7,621,961 B2 | 11/2009 | Stone et al. | |
| 7,758,650 B2 | 7/2010 | Dews et al. | |
| 7,802,503 B2 | 9/2010 | Couvillion et al. | |
| 7,819,923 B2 | 10/2010 | Stone et al. | |
| 7,998,217 B1 | 8/2011 | Brown | |
| 8,062,376 B2 | 11/2011 | Shultz et al. | |
| 8,070,820 B2 | 12/2011 | Winslow et al. | |
| 8,231,684 B2 | 7/2012 | Mutchler et al. | |
| 8,236,059 B2 | 8/2012 | Stone et al. | |
| 8,257,363 B2 | 9/2012 | Splieth et al. | |
| 8,357,204 B2 | 1/2013 | Ragbir | |
| 8,512,410 B2 | 8/2013 | Metcalfe et al. | |
| 8,529,629 B2 | 9/2013 | Angibaud et al. | |
| 8,545,504 B2 | 10/2013 | Durand-Allen et al. | |
| 8,608,805 B2 | 12/2013 | Forrer et al. | |
| 8,623,092 B2 | 1/2014 | Bickley et al. | |
| 8,647,387 B2 | 2/2014 | Winslow | |
| 8,663,333 B2 | 3/2014 | Metcalfe et al. | |
| 8,663,334 B2 | 3/2014 | Viscardi et al. | |
| 8,764,845 B2 | 7/2014 | Brooks et al. | |
| 8,764,846 B2 | 7/2014 | Grappiolo | |
| 8,795,379 B2 | 8/2014 | Smith et al. | |
| 8,888,855 B2 | 11/2014 | Roche et al. | |
| 8,906,103 B2 | 12/2014 | Stone et al. | |
| 8,945,234 B2 | 2/2015 | Humphrey | |
| 9,241,803 B2 | 1/2016 | Stone et al. | |
| 9,283,083 B2 | 3/2016 | Winslow et al. | |
| 9,326,862 B2 | 5/2016 | Smith et al. | |
| 9,421,105 B2 | 8/2016 | Metcalfe et al. | |
| 9,474,618 B2 | 10/2016 | Bickley et al. | |
| 9,498,344 B2 | 11/2016 | Hodorek et al. | |
| 9,566,162 B2 | 2/2017 | Isch | |
| 9,597,190 B2 | 3/2017 | Chavarria et al. | |
| 9,603,712 B2 | 3/2017 | Bachmaier | |
| 9,610,165 B2 | 4/2017 | Poncet et al. | |
| 9,622,869 B2 | 4/2017 | Nerot et al. | |
| 9,700,423 B2 | 7/2017 | Stone et al. | |
| 9,770,334 B2 | 9/2017 | Wiley et al. | |
| 9,844,439 B2* | 12/2017 | Katrana ............... A61F 2/4014 | |
| 9,867,710 B2 | 1/2018 | Dalla Pria et al. | |
| 9,925,047 B2 | 3/2018 | Klotz et al. | |
| 9,956,083 B2 | 5/2018 | Humphrey | |
| 10,034,759 B2 | 7/2018 | Deransart et al. | |
| 10,143,558 B2 | 12/2018 | Frankle | |
| 10,143,559 B2 | 12/2018 | Ries et al. | |
| 10,172,714 B2 | 1/2019 | Hatzidakis et al. | |
| 10,226,349 B2 | 3/2019 | Sperling et al. | |
| 10,383,734 B2 | 8/2019 | Ekelund et al. | |
| 10,433,967 B2 | 10/2019 | Deransart et al. | |
| 10,548,737 B2 | 2/2020 | Hodorek et al. | |
| 2001/0010023 A1* | 7/2001 | Schwartz ............ A61B 17/064 | 623/23.72 |
| 2001/0011193 A1 | 8/2001 | Nogarin | |
| 2002/0156534 A1 | 10/2002 | Grusin et al. | |
| 2003/0028253 A1 | 2/2003 | Stone et al. | |
| 2003/0097183 A1 | 5/2003 | Rauscher et al. | |
| 2004/0064190 A1 | 4/2004 | Ball et al. | |
| 2004/0230311 A1 | 11/2004 | Cyprien et al. | |
| 2005/0071014 A1 | 3/2005 | Barnett et al. | |
| 2006/0020344 A1 | 1/2006 | Shultz et al. | |
| 2006/0069445 A1 | 3/2006 | Ondrla et al. | |
| 2007/0162140 A1 | 7/2007 | McDevitt | |
| 2007/0173945 A1 | 7/2007 | Wiley et al. | |
| 2007/0179624 A1 | 8/2007 | Stone et al. | |
| 2007/0225821 A1 | 9/2007 | Reubelt et al. | |
| 2007/0244565 A1 | 10/2007 | Stchur | |
| 2008/0183297 A1 | 7/2008 | Boileau et al. | |
| 2008/0228281 A1 | 9/2008 | Forrer et al. | |
| 2009/0265010 A1 | 10/2009 | Angibaud et al. | |
| 2009/0281630 A1 | 11/2009 | Delince et al. | |
| 2010/0049327 A1* | 2/2010 | Isch ..................... A61F 2/34 | 623/19.12 |
| 2010/0114326 A1 | 5/2010 | Winslow et al. | |
| 2010/0268232 A1 | 10/2010 | Betz et al. | |
| 2010/0288421 A1 | 11/2010 | Kujawski et al. | |
| 2011/0029089 A1 | 2/2011 | Giuliani et al. | |
| 2011/0060417 A1 | 3/2011 | Simmen et al. | |
| 2011/0125285 A1 | 5/2011 | Ragbir | |
| 2012/0143204 A1 | 6/2012 | Blaycock et al. | |
| 2012/0253350 A1 | 10/2012 | Anthony et al. | |
| 2012/0253467 A1 | 10/2012 | Frankle | |
| 2013/0090736 A1 | 4/2013 | Katrana et al. | |
| 2013/0197652 A1 | 8/2013 | Ekelund et al. | |
| 2013/0289738 A1 | 10/2013 | Humphrey | |
| 2013/0325134 A1 | 12/2013 | Viscardi et al. | |
| 2014/0121709 A1 | 5/2014 | Gonzalez-Hernandez | |
| 2015/0190237 A1 | 7/2015 | Bonin, Jr. et al. | |
| 2015/0238324 A1 | 8/2015 | Nebosky et al. | |
| 2015/0245912 A1 | 9/2015 | Link | |
| 2015/0265411 A1 | 9/2015 | Deransart et al. | |
| 2016/0213480 A1 | 7/2016 | Stone et al. | |
| 2016/0262902 A1 | 9/2016 | Winslow et al. | |
| 2016/0361173 A1 | 12/2016 | Reubelt et al. | |
| 2017/0043052 A1 | 2/2017 | San Antonio et al. | |
| 2017/0049573 A1 | 2/2017 | Hodorek et al. | |
| 2017/0056187 A1 | 3/2017 | Humphrey et al. | |
| 2017/0030449 A1 | 11/2017 | Deransart et al. | |
| 2018/0000598 A1 | 1/2018 | Amis et al. | |
| 2018/0280152 A1 | 10/2018 | Mutchler et al. | |
| 2018/0333265 A1 | 11/2018 | Termanini et al. | |
| 2019/0046326 A1 | 2/2019 | Ball | |

(56) References Cited

U.S. PATENT DOCUMENTS

| | | |
|---|---|---|
| 2019/0105169 A1 | 4/2019 | Sperling |
| 2019/0231540 A1 | 8/2019 | Kim et al. |
| 2019/0231544 A1 | 8/2019 | Boileau et al. |

FOREIGN PATENT DOCUMENTS

| | | |
|---|---|---|
| DE | 102008010478 A1 | 8/2009 |
| EP | 0898946 A1 | 3/1999 |
| EP | 1093777 | 4/2001 |
| EP | 1402854 A2 | 3/2004 |
| EP | 1472999 A1 | 3/2004 |
| EP | 1415621 A2 | 5/2004 |
| EP | 1 520 562 | 4/2005 |
| EP | 1520560 B1 | 10/2006 |
| EP | 1782765 | 5/2007 |
| EP | 1048274 | 9/2012 |
| EP | 2 604 227 | 6/2013 |
| EP | 2604225 A1 | 6/2013 |
| FR | 2652498 A1 | 4/1991 |
| FR | 2 758 256 | 7/1998 |
| FR | 2773469 A1 | 7/1999 |
| FR | 2 932 678 | 12/2011 |
| FR | 3 025 089 | 3/2016 |
| GB | 1 504 055 | 3/1978 |
| JP | 2004-121850 | 4/2004 |
| JP | 2006-095300 | 4/2006 |
| WO | WO 93/09733 A1 | 5/1993 |
| WO | WO 96/17553 | 6/1996 |
| WO | WO 00/74554 | 12/2000 |
| WO | WO 2003/005933 | 1/2003 |
| WO | WO 2004/080331 | 9/2004 |
| WO | WO 2006/126238 | 11/2006 |
| WO | WO 2007/084939 | 7/2007 |
| WO | WO 2007/082925 | 10/2007 |
| WO | WO 2008/000928 A2 | 1/2008 |
| WO | WO 2008/050091 | 5/2008 |
| WO | WO 2008/109751 | 9/2008 |
| WO | WO 2013/064569 | 5/2013 |
| WO | WO 2014/067961 | 5/2014 |
| WO | WO 2014/178706 | 11/2014 |
| WO | WO 2015/112307 | 7/2015 |
| WO | WO 2016/094739 | 6/2016 |
| WO | WO 2017/184792 | 10/2017 |
| WO | WO 2019/053576 | 3/2019 |
| WO | WO 2006/106276 | 6/2019 |
| WO | WO 2019/106277 | 6/2019 |
| WO | WO 2019/178104 | 9/2019 |

OTHER PUBLICATIONS

Biomet Orthopedics, "Comprehensive® Shoulder System, Surgical Technique", 2007.
Delta, Delta CTA Reverse Shoulder Prosthesis, Surgical Technique, DePuy a Johnson & Johnson company, 2004.
Depuy, "Global™ Fx Shoulder Fracture System, Surgical Technique", 1999.
Depuy Synthes, "Global® UNITE Platform Shoulder System, Product Rationale & Surgical Technique", 2013.
DJO Surgical, "DJO Surgical Shoulder Solutions—Reaching Higher by Design", 2013.
Exactech, "Equinoxe Platform Shoulder System", 2014.
FH Orthopedics, "ARROW, Prothese d'epaule Universelle (Universal shoulder prosthesis)", Nov. 2009.
Integra, Titan™ Reverse Shoulder System, Surgical Technique, 2013.
JRI Orthopaedics, "VAIOS® Shoulder System", Mar. 6, 2011.
Levy et al., "Reverse Shoulder Prosthesis for Acute Four-Part Fracture: Tuberosity Fixation Using a Horseshoe Graft", J Orthop Trauma, vol. 25, No. 5, May 2011.
Stryker Orthopaedics, "ReUnion Fracture System Surgical Protocol", 2007.
Tornier, "Aequalis Ascend Flex Convertible Shoulder System", Feb. 8, 2016.
Zimmer, "Anatomical Shoulder™ Fracture System, Surgical Technique", 2010.
Zimmer®, "Trabecular Metal™ Humeral Stem—Enabling fracture healing", 2009.
Aston® Medical, "Operative Technique—Duocentric Expert Reversed,Total Shoulder Prosthesis".
Lima Corporate, "SMR System, Surgical Technique".
Mathys European Orthopaedics, "Affinis® Fracture Affinis® Fracture Inverse, Technique operatoire".
Tornier, "Aequalis-Fracture Shoulder Prosthesis", May 2017.
Tornier, "Aequalis® Reversed Adapter, Surgical Technique Shoulder Revision System", Nov. 2007.
Tornier, "Aequalis® Reversed Fracture, Surgical Technique Reversed Shoulder Prosthesis", Dec. 2008.

\* cited by examiner

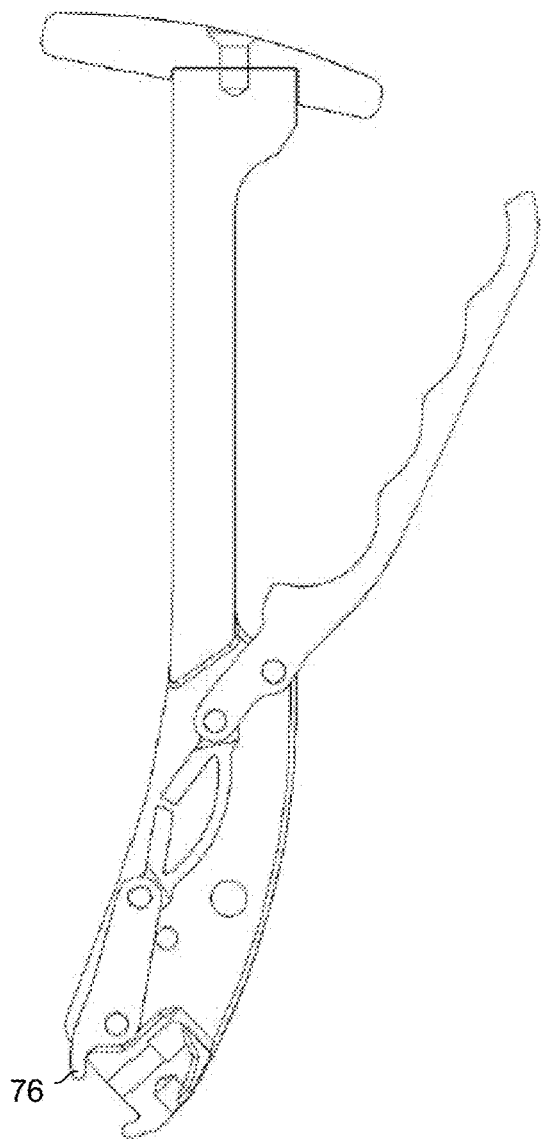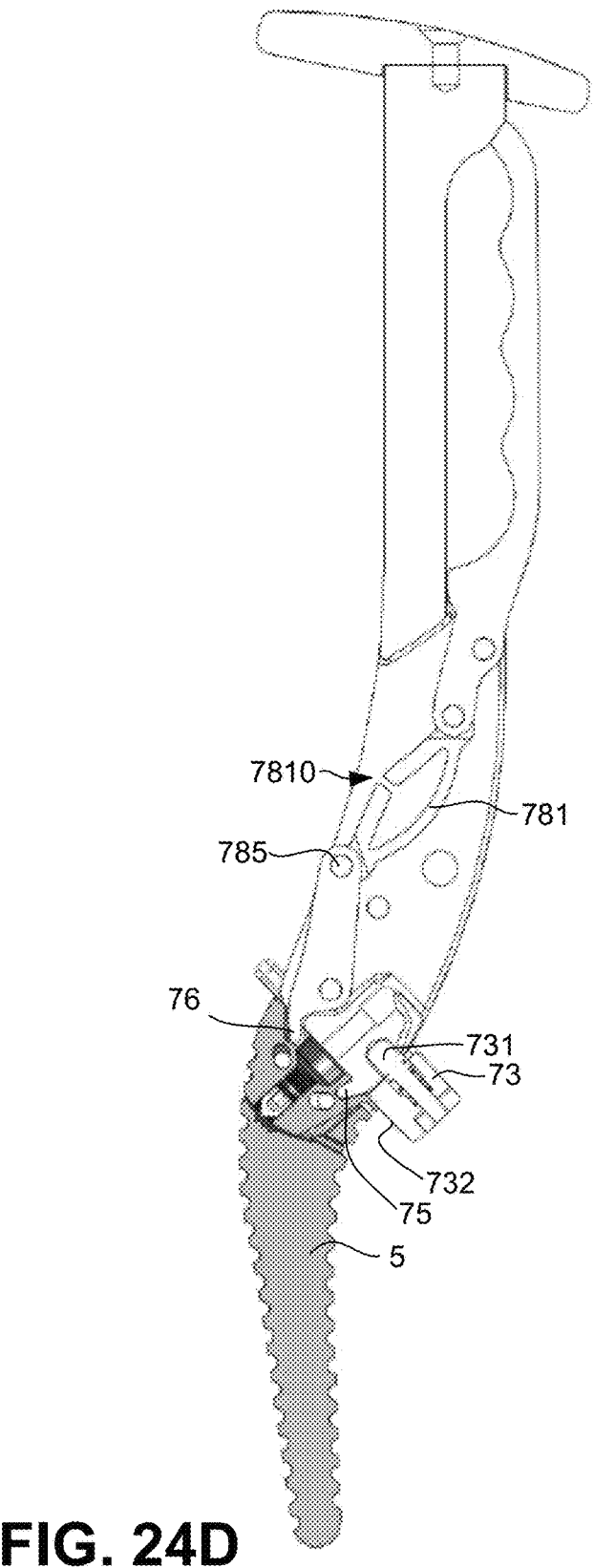
FIG. 24C
FIG. 24D

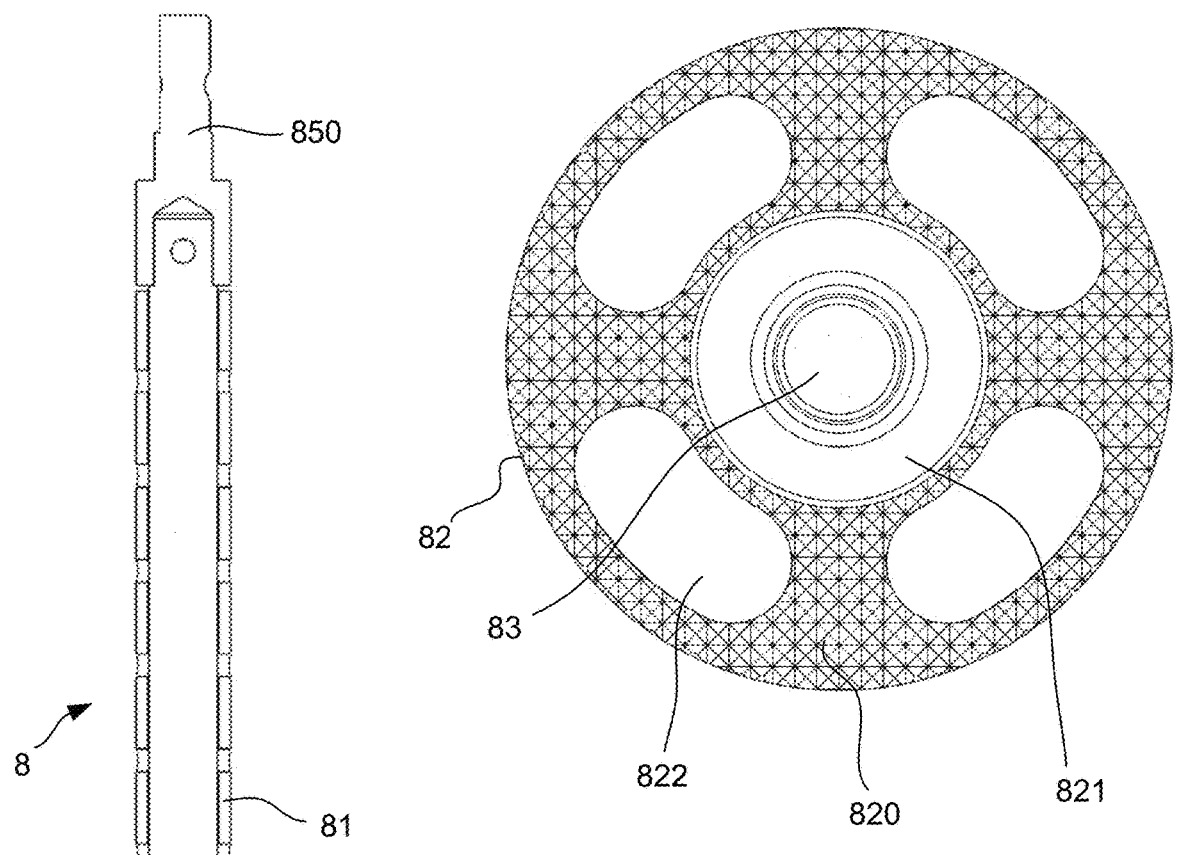
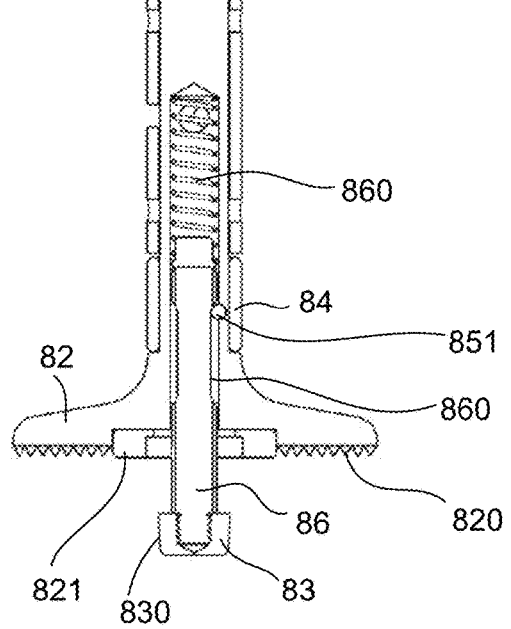
FIG. 26A
FIG. 26B

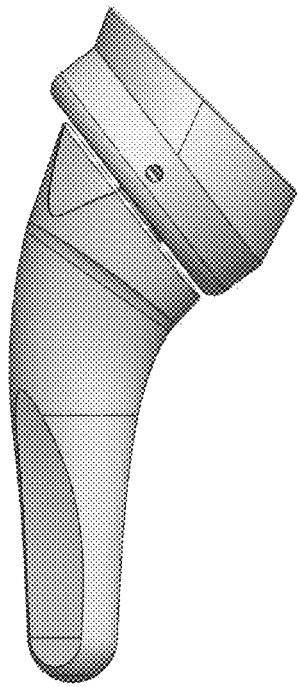
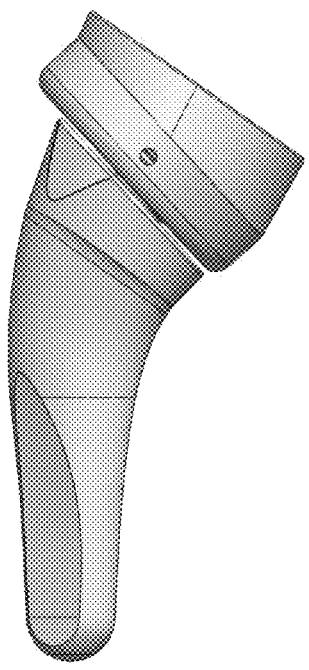
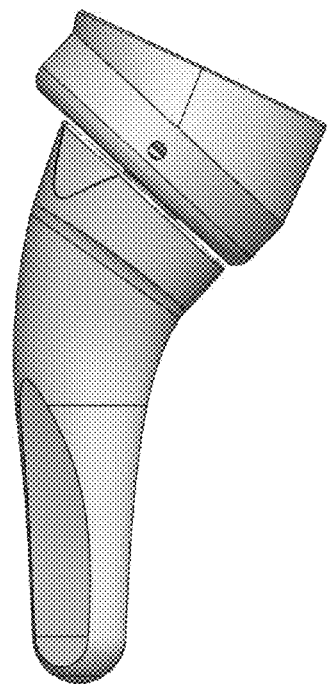
FIG. 35     FIG. 36     FIG. 37
| Stem Angle | Insert Angle | Reversed Construct Angle |
|---|---|---|
| 127.5 | 7.5 | 135 |
| 127.5 | 12.5 | 140 |
| 132.5 | 7.5 | 140 |
| 127.5 | 17.5 | 145 |
| 132.5 | 12.5 | 145 |
| 137.5 | 7.5 | 145 |
| 132.5 | 17.5 | 150 |
| 137.5 | 12.5 | 150 |
| 137.5 | 17.5 | 155 |
FIG. 38

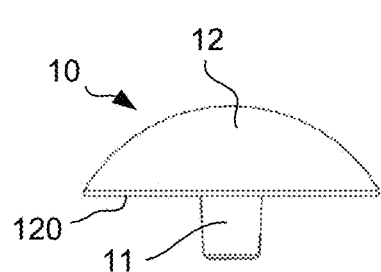 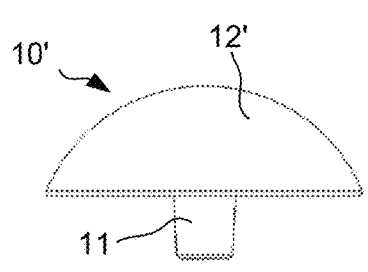 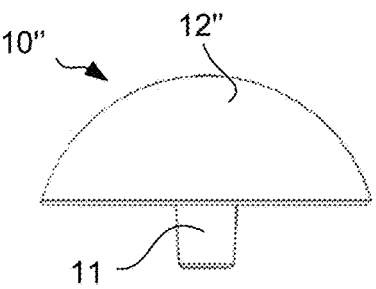
FIG. 38B  FIG. 38C  FIG. 38D
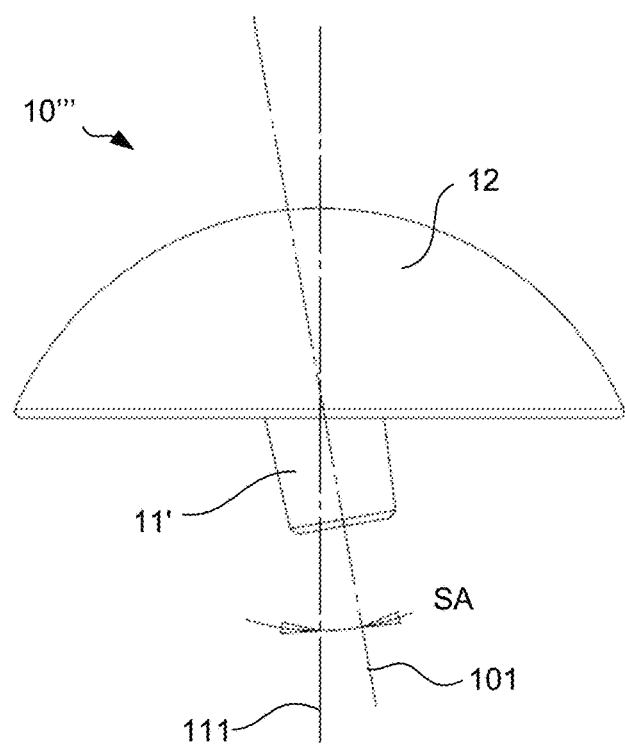
FIG. 38E

SYSTEMS FOR REVERSE SHOULDER IMPLANTS

CROSS-REFERENCE TO RELATED APPLICATIONS

This application is a continuation of U.S. patent application Ser. No. 14/432,463, filed Mar. 30, 2015, now U.S. Pat. No. 9,498,344, which is a national stage application based on International Application No. PCT/EP2013/072634, filed Oct. 29, 2013, which claims the benefit of U.S. Provisional Patent Application Ser. No. 61/719,835, filed on Oct. 29, 2012, which is incorporated by reference herein in its entirety for all purposes.

TECHNICAL FIELD

Embodiments of the present invention relate generally to shoulder prostheses, and more specifically to reverse shoulder prostheses.

BACKGROUND

Arthroplasty is the standard of care for the treatment of shoulder joint arthritis. A typical humeral head replacement which attempts to mimic anatomic conditions involves a metallic humeral stem and a modular head replacement, capable of multiple positions for optimal bony coverage. Such humeral head replacement might articulate with the native bone or an opposing glenoid resurfacing device, which may be manufactured from UHMWPE or any other acceptable material. Such humeral stem is usually offered in one or several inclination angles ranging from 125 degrees to 140 degrees.

For more severe cases of shoulder arthritis, the standard treatment is a reverse reconstruction, which includes reversing the kinematics of the shoulder joint. This is performed by securing a semi-spherical device to the glenoid, referred to as a glenoid sphere, and implanting a humeral stem with a modular cavity capable of receiving the glenoid sphere. The humeral stem is usually offered in one fixed inclination angle between 135 degrees and 155 degrees, with 155 degrees being the angle currently preferred by a majority of surgeons.

As patient disease may progress after anatomic treatment, revision surgery may be necessary to perform a reverse reconstruction of the shoulder. Removal of anatomic devices that have integrated into the patient's bony anatomy may prove to be difficult for the surgeon, and could potentially cause excessive patient bone loss.

SUMMARY

Embodiments of the present invention include a convertible prosthesis that is capable of conversion from a humeral head replacement to a reverse reconstruction without any removal of parts integrated into the patient's bony anatomy (e.g. implant stems). A desired overall implant inclination angle may be achieved by matching various implant stems with various reverse inserts, thus permitting a resection surface to be matched with an implant stem selection while also permitting a desired overall implant inclination angle to be achieved through the selection of an appropriate insert.

A modular reverse shoulder prosthesis according to some embodiments of the present invention includes a stem having a proximal taper and a primary center axis, the proximal taper extending into the stem about a taper axis; a tray having a distal taper configured to mate with the proximal taper of the stem, the tray having a proximal cavity with an inner sidewall; an insert having a distal end and a proximal end, the distal end having an outer sidewall configured to engage the inner sidewall of the tray, the outer sidewall being at least partially cylindrical and formed about an insert axis, the proximal end having an articular surface formed at least partially about a center of rotation, wherein the center of rotation is offset from the insert axis.

The prosthesis, wherein the center of rotation is offset from the insert axis in a direction toward a thinnest portion of the insert.

The prosthesis, wherein the center of rotation is offset from the insert axis by five to eight millimeters.

The prosthesis, wherein the center of rotation is offset from the insert axis by five to eight millimeters.

The prosthesis, wherein the center of rotation is offset from the primary center axis by twenty-two to twenty-eight millimeters when the tray is mated with the stem and the insert is engaged with the tray.

The prosthesis, wherein the insert is engageable with the proximal cavity of the tray at any rotational position of the insert about the first insert axis.

The system, wherein the insert is a first insert, wherein the distal end is a first distal end, wherein the proximal end is a first proximal end, wherein the concave articular surface is a first concave articular surface, and wherein the insert axis is a first insert axis, the system further comprising: a second insert having a second distal end configured to engage the proximal cavity of the tray, a second proximal end having a second concave articular surface, and a second insert axis that is normal to the second proximal end; wherein a third implantable combination of the first stem, the tray, and the second insert has a third overall inclination angle formed between the first primary center axis and the second insert axis, and wherein the first overall inclination angle is different from the third overall inclination angle.

The system, wherein a fourth implantable combination of the second stem, the tray, and the second insert has a fourth overall inclination angle formed between the second primary center axis and the second insert axis, and wherein the fourth overall inclination angle is different from the first overall inclination angle.

The system, wherein the fourth overall inclination angle is also different from the second overall inclination angle.

The system, wherein the third overall inclination angle is the same as the second overall inclination angle.

The system, wherein the fourth overall inclination angle is at least ten degrees different from the first overall inclination angle.

The system, further comprising a third stem having a third proximal taper and a third primary center axis, the third proximal taper extending into the third stem about a third taper axis, a third stem inclination angle formed between the third primary center axis and the third taper axis, wherein the third stem inclination angle is different from both the first and second stem inclination angles, and wherein the distal taper of the tray is further configured to mate with the third proximal taper of the third stem.

The system, further comprising a third insert having a third distal end configured to engage the proximal cavity of the tray, a third proximal end having a third concave articular surface, and a third insert axis that is normal to the third proximal end, wherein a fourth implantable combination of the first stem, the tray, and the third insert has a fourth overall inclination angle formed between the first primary center axis and the third insert axis, and wherein the fourth overall inclination angle is different from both the first overall inclination angle and the third overall inclination angle.

The system, further comprising a third insert having a third distal end configured to engage the proximal cavity of the tray, a third proximal end having a third concave articular surface, and a third insert axis that is normal to the third proximal end, wherein a fourth implantable combination of the first stem, the tray, and the third insert has a fourth overall inclination angle formed between the first primary center axis and the third insert axis, and wherein the fourth overall inclination angle is different from both the first overall inclination angle and the third overall inclination angle.

The system, any of the first, second, and third stems are combinable with the tray and any of the first, second, and third inserts to form implantable combinations having at least five different overall inclination angles formed between the primary center axis of a selected one of the first, second, and third stems and the insert axis of a selected one of the first, second, and third inserts.

The system, wherein the at least five different overall inclination angles include 135°, 140°, 145°, 150°, and 155°.

The system, wherein the at least five different overall inclination angles are each separated from each other by at least five degrees The system, wherein two or more different implantable combinations can be formed with one of the first, second, and third stems, the tray, and one of the first, second, and third inserts, to arrive at the same overall inclination angle.

The system, wherein the distal end has an outer sidewall configured to engage an inner sidewall of the tray, the outer sidewall being at least partially cylindrical and formed about the insert axis, wherein the concave articular surface is formed at least partially about a center of rotation, and wherein the center of rotation is offset from the insert axis.

The system, wherein the first distal end has a first outer sidewall configured to engage an inner sidewall of the tray, the first outer sidewall being at least partially cylindrical and formed about the first insert axis, wherein the first concave articular surface is formed at least partially about a first center of rotation, wherein the first center of rotation is offset from the insert axis, wherein the second distal end has a second outer sidewall configured to engage the inner sidewall of the tray, the second outer sidewall being at least partially cylindrical and formed about the second insert axis, wherein the second concave articular surface is formed at least partially about a second center of rotation, and wherein the second center of rotation is offset from the second insert axis.

The system, wherein the first center of rotation is offset from the first insert axis toward a thinnest portion of the first insert, and wherein the second center of rotation is offset from the second insert axis toward a thinnest portion of the second insert.

The system, wherein the distal taper is formed about a taper axis, and wherein the taper axis is offset from the insert axis when the insert is inserted into the tray, so as to permit eccentric rotation of the tray about the taper axis when the distal taper is inserted into the proximal taper of the stem.

The system, wherein the first insert is engageable with the proximal cavity of the tray at any rotational position of the first insert about the first insert axis, and wherein the second insert is engageable with the proximal cavity of the tray at any rotational position of the second insert about the second insert axis.

The system, wherein the fins are configured to secure the insert against rotation about the insert axis regardless of the rotational position of the insert about the insert axis when the insert is inserted into the tray.

The system, wherein the proximal cavity includes an inner sidewall, wherein the distal end of the insert includes an outer sidewall configured to engage the inner sidewall of the tray, the outer sidewall being at least partially cylindrical and having the outer diameter formed about the insert axis, the fins projecting inwardly from the inner sidewall of the tray, the fins projecting to an inner diameter that is smaller than the outer diameter of the outer sidewall.

The system, wherein the fins deform the insert by cutting the insert when the insert is inserted into the tray.

The system, wherein the fins deform the insert by inelastically deforming the insert when the insert is inserted into the tray.

The system, wherein the fins are at least three fins arranged on the inner sidewall in a rotationally symmetrical manner about the insert axis.

The system, wherein the at least three fins are at least six fins arranged on the inner sidewall in the rotationally symmetrical manner about the insert axis.

The system, wherein a first material out of which the fins are made is harder than a second material out of which the distal end of the insert is made.

The system, wherein the distal taper is formed about a taper axis, and wherein the taper axis is offset from the insert axis when the insert is inserted into the tray, so as to permit eccentric rotation of the tray about the taper axis when the distal taper is inserted into the proximal taper of the stem.

The system, wherein the fins project inwardly from a bottom of the proximal cavity.

The system, wherein the insert includes a first channel formed circumferentially about the distal end, wherein the insert further includes a snap-fit ring seated at least partially within the first channel, and wherein the tray includes a second channel formed circumferentially within the proximal cavity, wherein the snap-fit ring is configured to become seated in both the first and second channels when the insert is inserted into the tray so as to secure the insert against separation from the tray.

The system, wherein the snap-fit ring has an at-rest configuration in which an inner diameter of the snap-fit ring is within the first channel and an outer diameter of the snap-fit ring is outside of the first channel, a compressed configuration in which the outer diameter of the snap-fit ring is seated fully within the first channel, and a partially compressed configuration in which the outer diameter is smaller than the outer diameter of the snap-fit ring in the compressed configuration but not entirely seated within the first channel; wherein the snap-fit ring is configured to be in the at-rest configuration prior to insertion of the insert into the tray, wherein the snap-fit ring is configured to be in the compressed configuration as the insert is initially inserted into the tray, and wherein the snap-fit ring is configured to assume the partially compressed configuration when the snap-fit ring is seated in both the first and second channels.

The system, wherein the snap-fit ring is configured to compress radially so as to be fully received within the first channel when the insert is first inserted into the tray.

The system, wherein the snap-fit ring includes a discontinuity to facilitate radial compression of the snap-fit ring when the insert is first inserted into the tray.

The system, wherein the snap-fit ring reversibly secures the insert against separation from the tray.

The system, wherein the tray includes one or more holes formed from an outer surface of the tray to within the second channel of the proximal cavity, wherein the one or more holes permit insertion of a tool to compress the snap-fit ring into the first channel so as to permit release of the insert from the tray.

The system, wherein the snap-fit ring is configured to compress radially, wherein the snap-fit ring includes a distal edge that is chamfered to facilitate compression of the snap-fit ring when the insert is inserted into the tray.

The system, wherein the tray includes a chamfered proximal edge configured to interact with the chamfered distal edge of the snap-fit ring.

The system, wherein the snap-fit ring is configured to compress radially so as to be fully received within the second channel when the insert is first inserted into the tray.

The system, wherein the snap-fit ring includes a discontinuity to facilitate radial compression of the snap-fit ring when the insert is first inserted into the tray.

The system, wherein the snap-fit ring reversibly secures the insert against separation from the tray.

The system, wherein the tray includes one or more holes formed from an outer surface of the tray to within the first channel of the proximal cavity, wherein the one or more holes permit insertion of a tool to compress the snap-fit ring into the second channel so as to permit release of the insert from the tray.

The system, wherein the snap-fit ring is configured to compress radially, wherein the snap-fit ring includes a distal edge that is chamfered to facilitate compression of the snap-fit ring when the insert is inserted into the tray.

The system, wherein the tray includes a chamfered proximal edge configured to interact with the chamfered distal edge of the snap-fit ring.

The system, wherein the snap-fit ring has an at-rest configuration in which an inner diameter of the snap-fit ring is within the second channel and an outer diameter of the snap-fit ring is outside of the second channel, a compressed configuration in which the outer diameter of the snap-fit ring is seated fully within the second channel, and a partially compressed configuration in which the outer diameter is smaller than the outer diameter of the snap-fit ring in the compressed configuration but not entirely seated within the second channel; wherein the snap-fit ring is configured to be in the at-rest configuration prior to insertion of the insert into the tray, wherein the snap-fit ring is configured to be in the compressed configuration as the insert is initially inserted into the tray, and wherein the snap-fit ring is configured to assume the partially compressed configuration when the snap-fit ring is seated in both the first and second channels.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 24C illustrates the partial cut-away front elevation view of the inserter of FIG. 24B in a partially closed position, according to embodiments of the present invention.

FIG. 24D illustrates the partial cut-away front elevation view of the inserter of FIGS. 24A and 24B in a closed position and engaged with a broach shown in cross section, according to embodiments of the present invention.

FIG. 26A illustrates a front cross-sectional view of the reamer device of FIGS. 25 and 26, according to embodiments of the present invention.

FIG. 26B illustrates a bottom plan view of the reamer blade of the reamer device of FIGS. 25-26A, according to embodiments of the present invention.

FIG. 35 illustrates a front elevation view of a stem, tray, and insert construct having a reverse construct angle of 135 degrees, according to embodiments of the present invention.

FIG. 36 illustrates a front elevation view of a stem, tray, and insert construct having a reverse construct angle of 145 degrees, according to embodiments of the present invention.

FIG. 37 illustrates a front elevation view of a stem, tray, and insert construct having a reverse construct angle of 155 degrees, according to embodiments of the present invention.

FIG. 38 illustrates a reversed construct angle chart, according to embodiments of the present invention.

FIG. 38B illustrates a front elevation view of an anatomical humeral head implant, according to embodiments of the present invention.

FIG. 38C illustrates a front elevation view of another anatomical humeral head implant, according to embodiments of the present invention.

FIG. 38D illustrates a front elevation view of yet another anatomical humeral head implant, according to embodiments of the present invention.

FIG. 38E illustrates a front elevation view of yet another anatomical humeral head implant with a stem angle formed between the stem and the humeral head portion, according to embodiments of the present invention.

Figure 1:
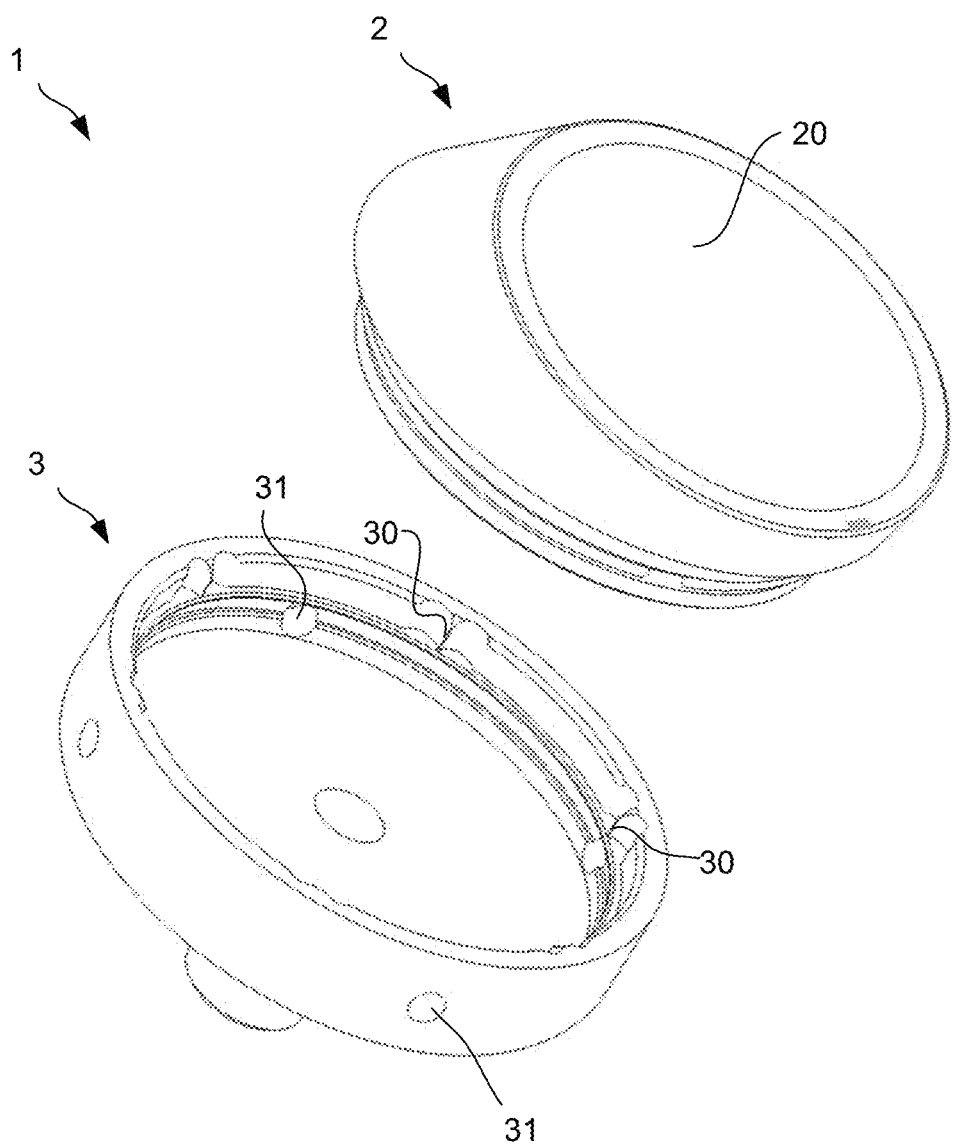
FIG. 1 illustrates an exploded perspective view of a tray and insert assembly, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 illustrates an exploded perspective view of an assembly 1 of a tray 3 and an insert 2, according to embodiments of the present invention. The assembly 1 forms part of a reverse shoulder prosthesis. In implanting such a reverse shoulder prosthesis, a humeral head is resected and a stem is implanted into the resected end of the humerus. The tray 3 is coupled with the stem, and the insert 2 is coupled with the tray 3. Because various types of inserts 2 may be used with tray 3, for example inserts with different shapes, sizes, and/or inclination angles, the insert 2 couples with the tray 3 in a snap-fit configuration once the desired insert 2 has been selected. The insert 2 may include an articular surface 20, for example a concave articular surface 20 that is configured to receive and abut a convex prosthetic head component or other head component for articulation therewith.

Figure 2:
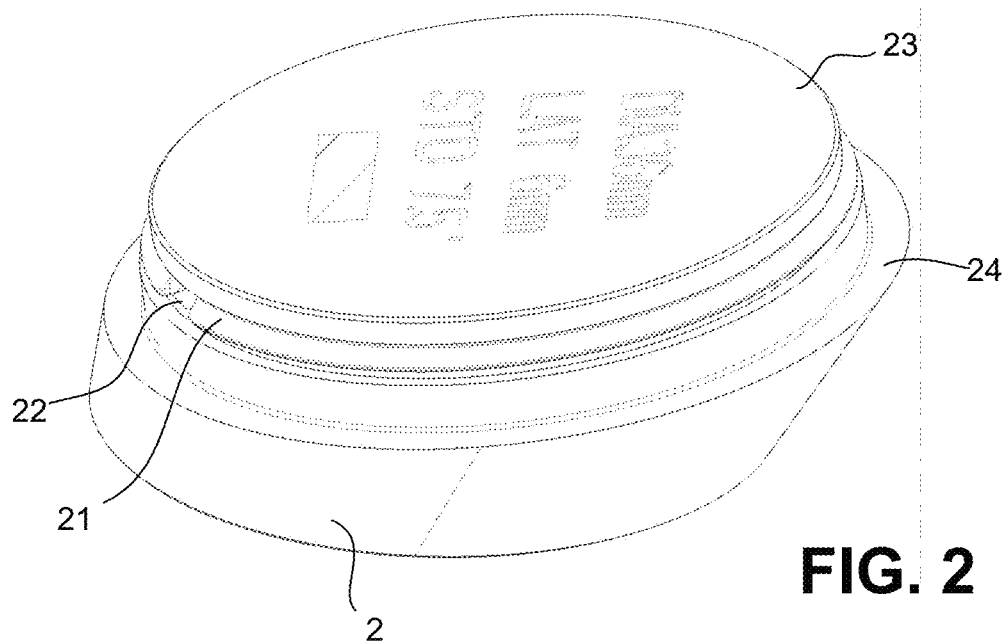
FIG. 2 illustrates a bottom perspective view of an insert, according to embodiments of the present invention.
Figure 3:
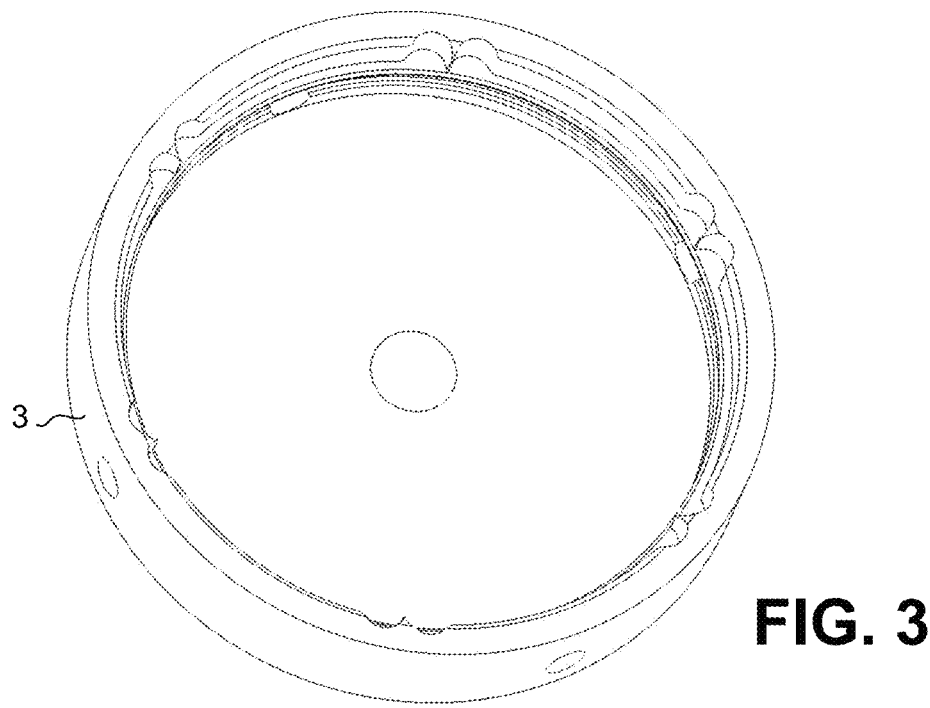
FIG. 3 illustrates a top perspective view of a tray, according to embodiments of the present invention.
Figure 4:
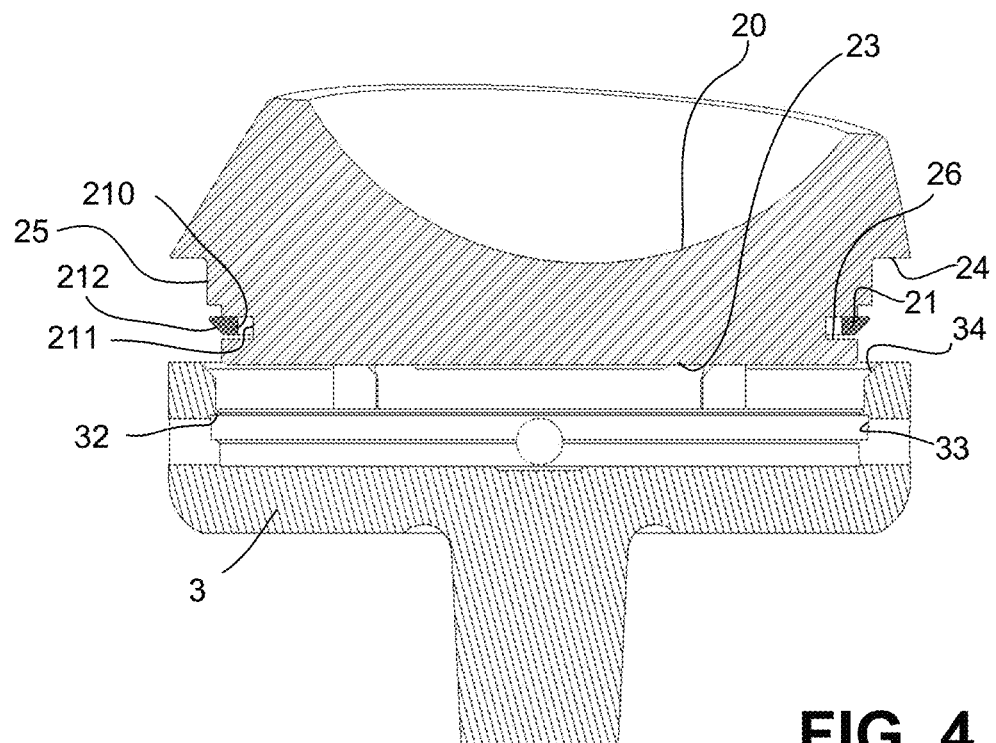
FIG. 4 illustrates a cross-sectional view of the tray and insert assembly of FIG. 1 before the insert has been affixed to the tray, according to embodiments of the present invention.

FIG. 2 illustrates a bottom perspective view of insert 2, according to embodiments of the present invention. FIG. 3 illustrates a top perspective view of a tray 3, according to embodiments of the present invention. FIG. 4 illustrates a cross-sectional view of the tray 3 and insert 2 before the insert 2 has been affixed to the tray 3, according to embodiments of the present invention. The insert 2 includes a snap-fit ring 21 seated within a channel 26. Ring 21 may be included with the insert 2 and seated in channel 26 when the insert 2 is packaged and/or shipped, as part of a kit for example. The ring 21 may have an irregular cross-sectional shape, for example the ring 21 may include a chamfered edge 212 which is configured to interact with a chamfered edge 34 of the tray 3 when the insert 2 is inserted into the tray 3. The outer diameter 211 of the channel 26 may be smaller than the inner diameter 210 of the ring 21, thereby permitting the ring 21 to become compressed within the channel 26 as the ring 21 passes edge 34 and edge 32 when insert 2 is inserted into tray 3. The ring 21 may also include a discontinuity 22 (see FIG. 2), which assists the ring 21 in compressing and becoming recessed within the channel 26. Alternatively, the ring 21 may be a continuous ring rather than a C-shaped ring. The inner diameter of 211 of the recess 26 being smaller than the inner diameter 210 of the snap-fit ring 21 also helps to keep the ring 21 centered with respect to the tray 3 and the insert 2. The channel 26 may be deep enough to fully accommodate the ring 21 when the ring is compressed.

Figure 6:
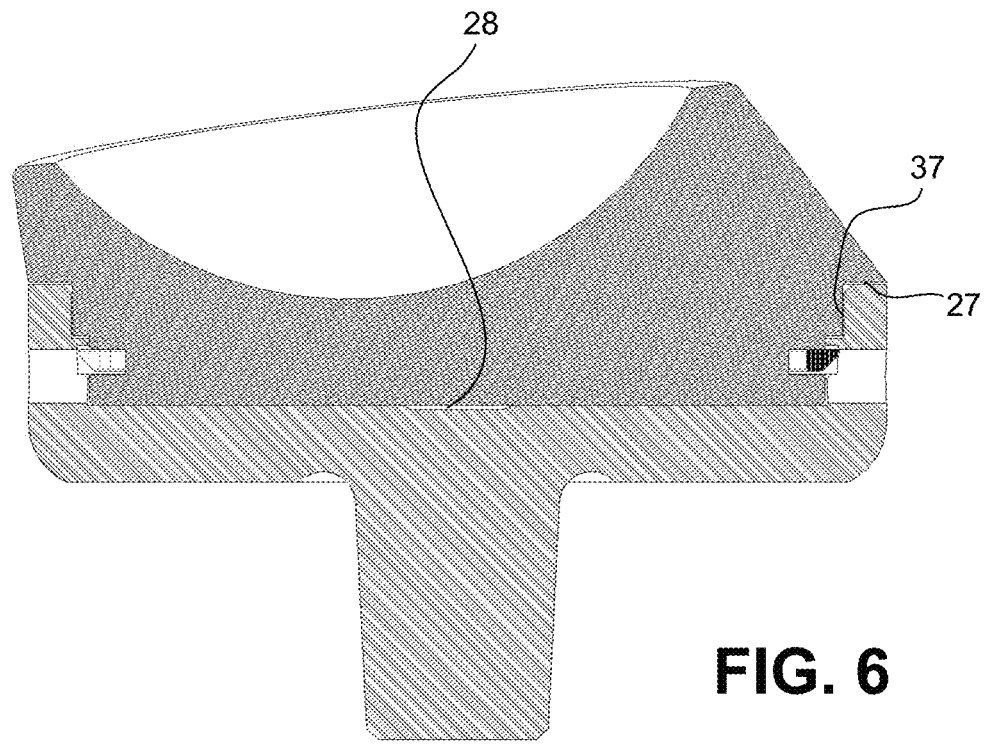
FIG. 6 illustrates a cross-sectional view of the tray and insert assembly of FIG. 4 with the insert affixed to the tray, according to embodiments of the present invention.

The tray 3 includes a channel 33 configured to receive the ring 21. At a proximal edge of the channel 33, a retaining ridge 32 extends inwardly. Due to the cross-sectional shape of ring 21, and the protrusion of retaining edge 32, when the insert 2 is inserted into the tray 3, the ring 21 compresses to clear retaining edge 32 but then expands back to its original diameter and/or shape within channel 33, which deters dislodgement of the insert 2 from the tray 3. The retaining edge 32 and/or channel 26 may be circular and may extend around an entire periphery of the insert 2, according to embodiments of the present invention. FIG. 6 shows the insert 2 and tray 3 in the locked position. In the locked position, the insert 2 remains snugly engaged with the tray 3 during movement and use of the implant by the patient. This locking, which may also be referred to as a snap-fit, of the insert 2 with the tray 3 may be reversible. For example, apertures 31 (see FIG. 1) are included in order to permit a tool to be inserted through the tray 3 from outside the tray 3 to compress the ring thereby loosening the insert 2 and pushing the insert 2 out of the tray 3.

Figure 5:
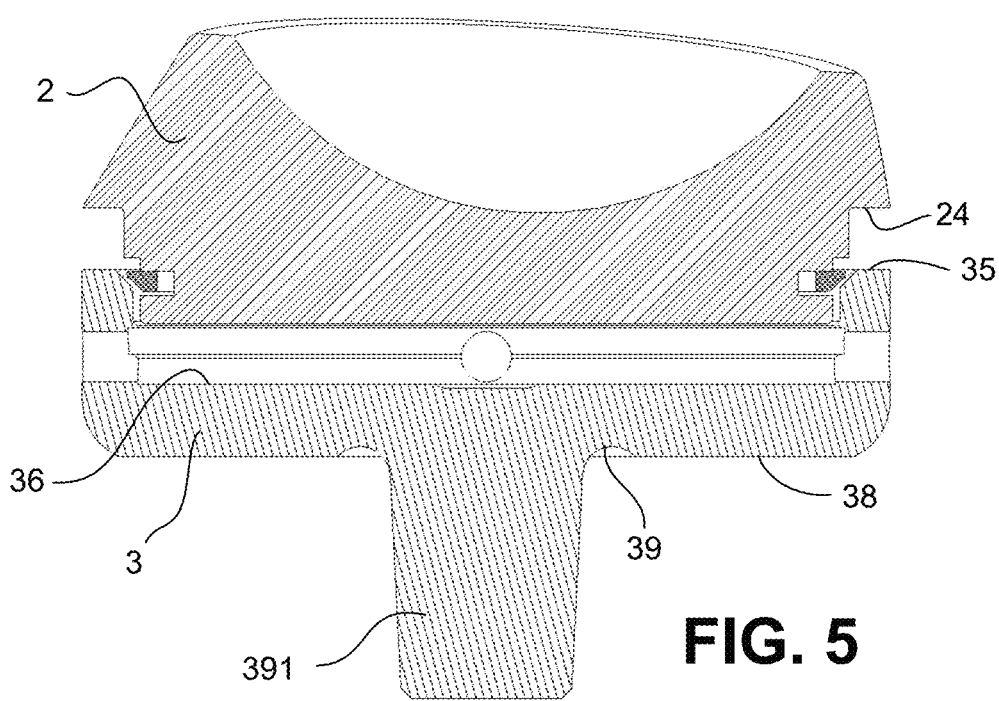
FIG. 5 illustrates the cross-sectional view of the tray and insert assembly of FIG. 4, as the insert is being affixed to the tray, according to embodiments of the present invention.
Figure 7:
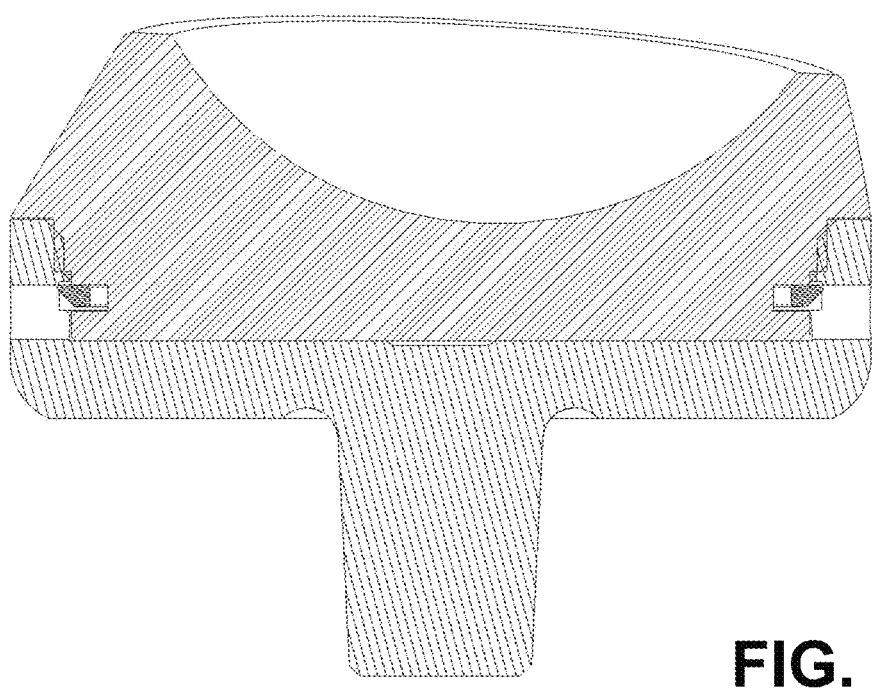
FIG. 7 illustrates the cross-sectional view of the tray and insert assembly of FIG. 4 with the insert affixed to the tray, according to embodiments of the present invention.

The snap-fit engagement of the insert 2 with the tray 3 maintains the insert 2 within the tray 3 after implantation. The tray 3 may also include fins 30 formed on an inner diameter of the tray 3. A sidewall portion 25 of the insert 2 may be cylindrical in shape, and may have an outer diameter 25 that is slightly larger than an inner diameter formed by the tips of fins 30. As such, when insert 2 is inserted into tray 3, the fins 30 interfere with the sidewall 25 in order to prevent rotation of the insert 2 with respect to the tray 3. In some embodiments, the fins 30 are of a stiffer or harder material than sidewall 25 and cut into the sidewall 30 in order to inhibit rotation. In other embodiments, the fins 30 and/or sidewall 25 deform in order to increase friction and/or gripping to inhibit rotation. The cross-sectional views of FIGS. 4, 5, and 7 are taken along a diameter that passes directly through the fins 30, and the overlap and/or interference between the fins 30 and the sidewall 25 is shown in FIG. 7. The cross-sectional view of FIG. 6 is taken along a diameter that does not pass through the fins 30.

Due to the configuration of the snap-fit ring 21 locking mechanism and fin 30 locking mechanism, the insert 2 may be locked to the tray 3 at any rotational angle of the insert 2 with respect to the tray 3. This performance may be referred to as "infinitely dialable," in other words, the insert 2 may be "dialed" or rotated to any desired rotational angle about the tray 3 and then locked to the tray 3.

The tray 3 may be made of metal, for example titanium. The insert 2 may be made of polymer, for example, polyethylene. The snap-fit ring may be made of an elastic material, for example titanium, titanium alloy, metal alloy, PEEK, and the like.

According to some embodiments of the present invention, a gap 27 is formed between an underside 24 of the insert 2 and a top surface 35 of the tray 3 when the insert 2 is fully seated in the tray 3. In other words, the bottom surface 23 of the insert 2 is always in contact with the bottom surface 36 of the tray 3, according to embodiments of the present invention. A recess 28, for example a circular recess 28, may be formed in the bottom surface 36, in order to accommodate a small lug due to material left on the insert 2 due to the machining process, according to embodiments of the present invention.

Figure 8:
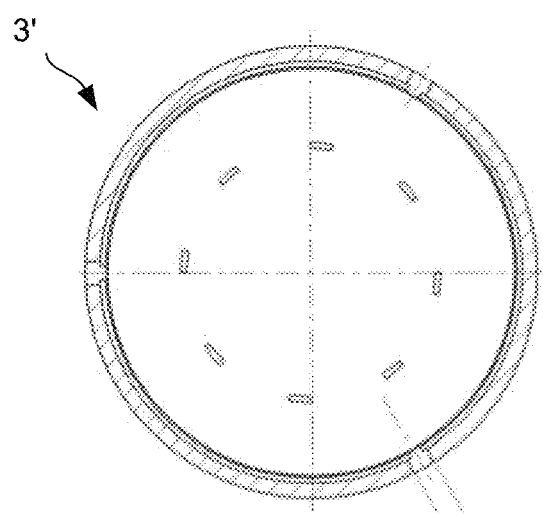
FIG. 8 illustrates a top plan view of an alternative tray, according to embodiments of the present invention.
Figure 9:
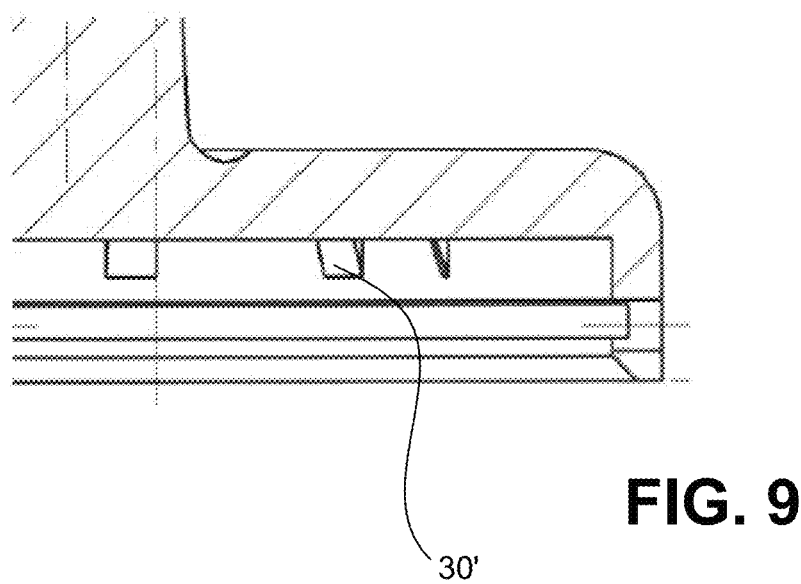
FIG. 9 illustrates a partial cross-sectional view of the alternative tray of FIG. 8, according to embodiments of the present invention.

FIGS. 8 and 9 illustrate an alternative tray 3', according to embodiments of the present invention. Tray 3' includes teeth 30' formed on a bottom surface of the tray 3', which interact with a bottom surface 23 of insert 2 to inhibit rotation of the insert 2 when insert 2 is inserted into snap-fit engagement with tray 3'. According to some embodiments of the present invention, a tray may include both teeth 30 around an inside sidewall periphery and teeth 30' protruding from a bottom surface of the tray.

According to some embodiments of the present invention, the insert 2 and snap-fit ring 21 are delivered pre-assembled. The snap-fit ring 21 may include an asymmetrical cross-sectional shape such that the ring 21 includes a chamfer 212 that cooperates with the chamfer 34 of the tray. The chamfer 212 or 34 angle may be forty-five degrees, for example. In some cases, the chamfer 212 or 34 angle may be forty to fifty degrees; in other cases, the angle may be thirty to sixty degrees, and in yet other cases this angle may be twenty to seventy degrees.

According to embodiments of the present invention, during at least one point in the assembly of the insert 2 to the tray 3, the ring 21 is fully recessed into the insert 2. According to some embodiments of the present invention, the retaining edge 32 is more than 0.1 and less than 0.5 millimeters thick. The inner diameter 211 of the channel 26 may be smaller than the inner diameter 210 of the ring 21, according to embodiments of the present invention. The teeth 30 may be cut into a peripheral internal diameter of the tray 3, and the outer diameter of the cylindrical sidewall 25 of the insert 2 is between 0.1 and 0.25 millimeters smaller than the inner diameter of the cylindrical portion 37 of the tray 3 with which the sidewall 25 interfaces when the insert 2 is locked into the tray 3. The inner diameter of the tips of teeth 30 may be 0.7 to 1.0 millimeters smaller than the outer diameter of the cylindrical sidewall 25 of the insert 2, according to embodiments of the present invention. The tray 3 may include a number of teeth spaced radially at equidistant angles, for example six teeth 30 spaced sixty degrees apart. According to embodiments of the present invention, the teeth 30 are 2.5 millimeters high. The residual gap 27 between surfaces 24 and 35 when the insert 2 is fully engaged with the tray 3 is no more than 0.4 millimeters, according to embodiments of the present invention. The recess 28 formed in the bottom 36 of the tray 3 may be 0.1 to 0.3 millimeters deep and may extend outwardly from a central axis to a diameter of less than six millimeters, according to embodiments of the present invention.

When making an anatomical cut in bone B, an implant stem must be implanted to match the resection angle of the resection surface R. This involves the use of instrumentation that measures the angle so the proper stem may be selected. Typically, this angle is read with an instrument connected to a reamer that is coaxial to the intramedullary canal. This approach may sometimes lead to inaccuracy, as the broach body may often fit differently in the cavity than the reamer. In other systems, the broach has marks that must be visually aligned with the resection surface, which may be prone to user error. Once the angle is determined, a trial is often assembled to match this angle. Often, this angle is incorrect, necessitating removal of the trial and insertion of a different assembly. These steps may often lead to inaccuracy and the increasing of operating time.

Figure 10:
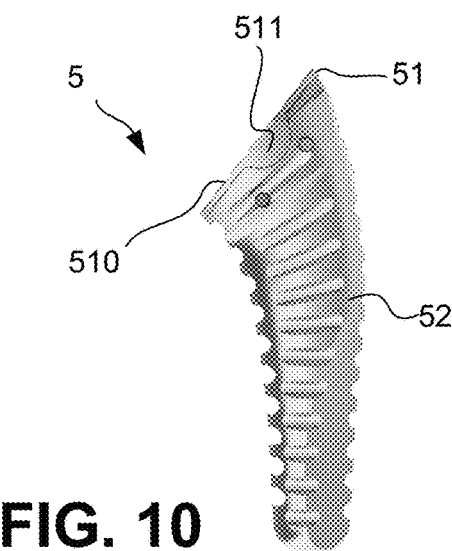
FIG. 10 illustrates a front elevation view of a broach, according to embodiments of the present invention.
Figure 11:
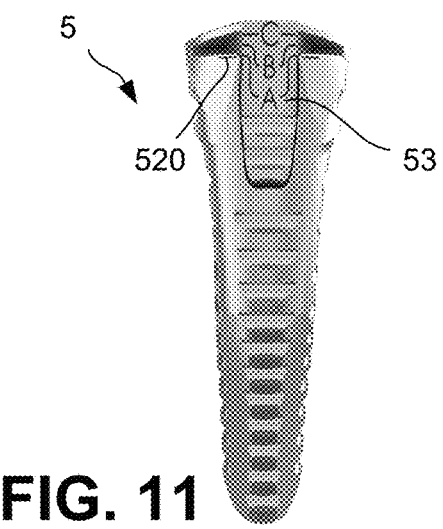
FIG. 11 illustrates a lateral elevation view of the broach of FIG. 10, according to embodiments of the present invention.

Broaches according to embodiments of the present invention include a pivoting neck that can be unlocked to allow movement between various angle selections. FIG. 10 illustrates a front elevation view of a broach 5, according to embodiments of the present invention. FIG. 11 illustrates a lateral elevation view of the broach 5, according to embodiments of the present invention. Broach 5 includes a proximal plate 51 having a proximal surface 510, the proximal plate 51 pivoting about a stem 52 about pivot point 511, according to embodiments of the present invention. The proximal plate 51 may be pivoted continuously between medial and lateral extents, but may be lockable to the stem 52 at a selected number of angles, for example three.

Figure 12:
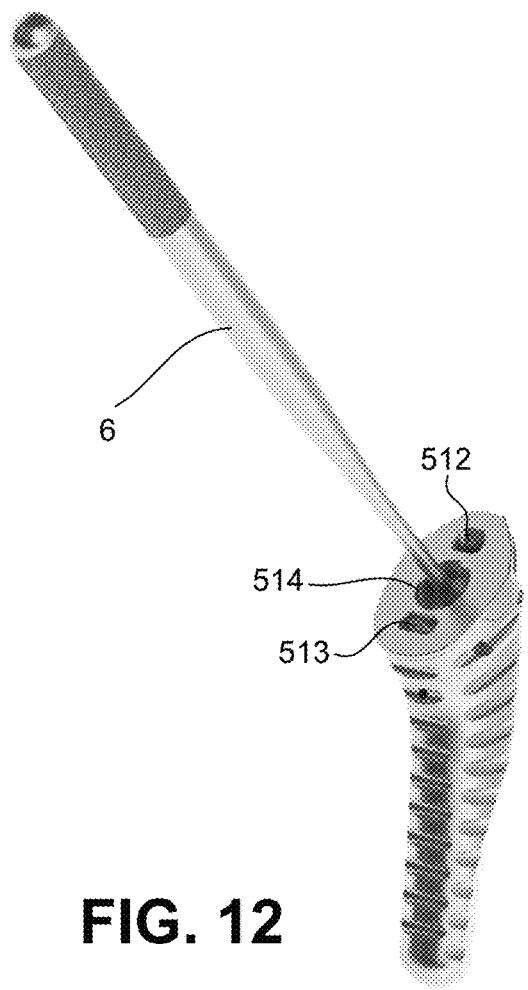
FIG. 12 illustrates a perspective view of a screwdriver adjusting an angle of a resection face of the broach of FIGS. 10 and 11, according to embodiments of the present invention.
Figure 13:
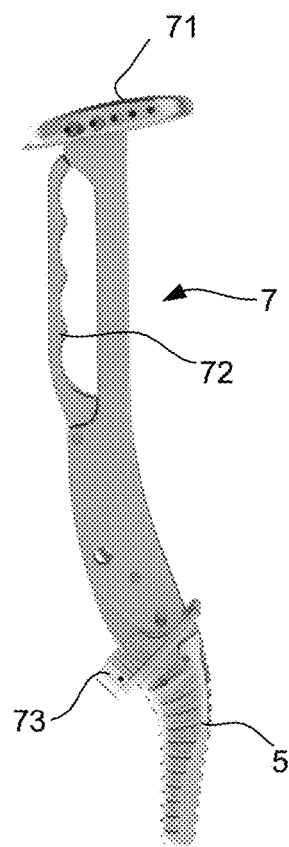
FIG. 13 illustrates a front elevation view of an inserter coupled with the broach of FIGS. 10 and 11, according to embodiments of the present invention.
Figure 12A:
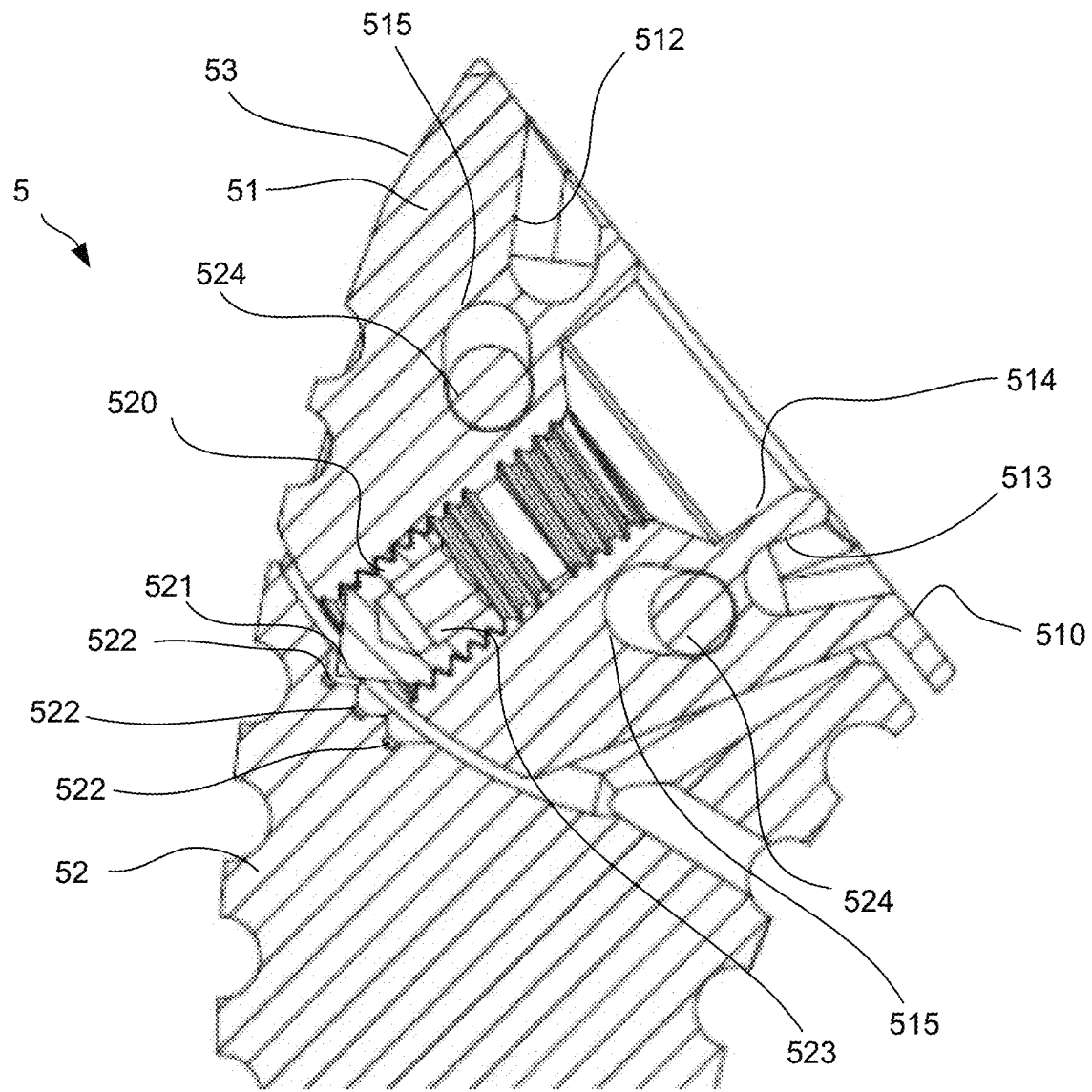
FIG. 12A illustrates an enlarged partial front cross-sectional view of the proximal portion of the broach of FIGS. 10 and 11, according to embodiments of the present invention.

As illustrated in greater detail in FIG. 12A, the stem 52 may include three pockets 522 under the proximal plate 51 configured to receive a tip 521 of a screw 520 placed through locking hole 514; the angle of the plate 51 may be locked with respect to the stem 52 by seating screw 520 through hole 514 and into one of the three angle pockets 522, for example using a screw driver 6 as shown in FIG. 12 by inserting the driver end of the screw driver through hole 514 and into mating engagement with a receptacle 523 on the set screw 520. The set screw 520 may be threadably engaged with a threaded inner portion of hole 514 as shown in FIG. 12A, such that it may be selectively, reversibly, and removably advanced into and out of engagement with one of the three pockets 522, with each of the three pockets 522 corresponding to a different inclination angle of the plate 51 face 510. The three pockets 522 may be shaped and/or placed so as to provide tactile feedback to the surgeon who is holding the driver tool 6 that is engaged with the set screw 520, in order to permit the surgeon to feel when the set screw 520 is seated in one of the pockets 522 to lock the plate 51 with respect to the stem 52. The screw 520 used for this locking may be a set screw 520 which remains in hole 514 during pivoting of the plate 51 with respect to stem 52, according to embodiments of the present invention. The stem 52 may include pegs 524 fixedly coupled with the stem 52, and the plate 51 may include slots 515 in which the pegs 524 slide in order to help constrain and limit the pivoting of the plate 51 with respect to the stem 52, according to embodiments of the present invention.

Figure 14:
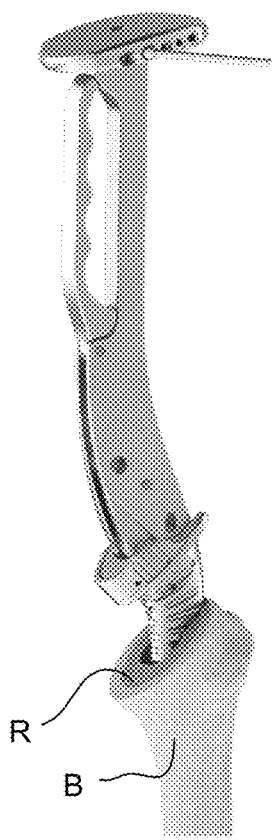
FIG. 14 illustrates a front perspective view of the inserter and broach assembly of FIG. 13 with the broach at least partially inserted into a bone cavity, according to embodiments of the present invention.

The lateral surface of the broach 5, as seen in FIG. 11, includes a reference mark 520 on the stem 52 and index marks 53 on the lateral surface of the plate 51 to indicate at which angle the plate 51 has been locked with respect to the stem 52. The plate 51 may include lateral and distal grooves 512, 513 configured to receive prongs for coupling to an inserter 7. Inserter 7 may be coupled to broach 5 and used to broach a cavity into the resected surface R of the bone B, as shown in FIG. 14.

Figure 15:
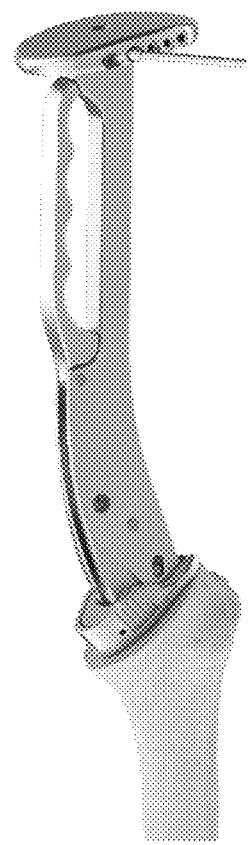
FIG. 15 illustrates a front perspective view of the inserter and broach assembly of FIG. 13 with the broach fully inserted into the bone cavity, according to embodiments of the present invention.
Figure 16:
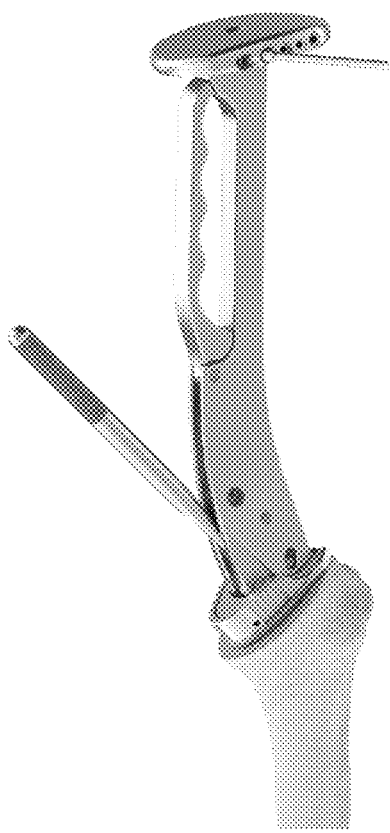
FIG. 16 illustrates a front perspective view of the inserter and broach assembly of FIG. 13 with the broach fully inserted into the bone cavity, and with a screwdriver being used to select the angle of the resection face of the broach, according to embodiments of the present invention.
Figure 17:
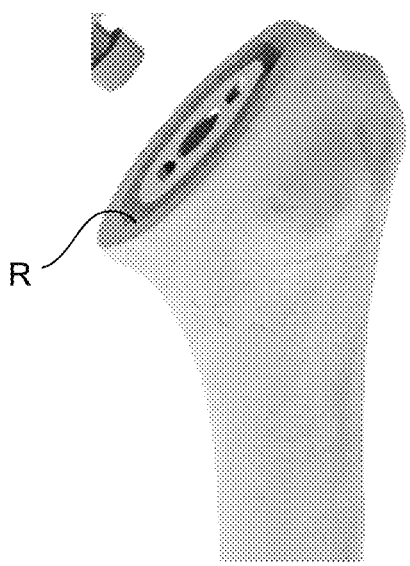
FIG. 17 illustrates a front perspective view of the broach of FIGS. 10 and 11 inserted into the bone hole and substantially flush with a resection surface of the bone, according to embodiments of the present invention.
Figure 18:
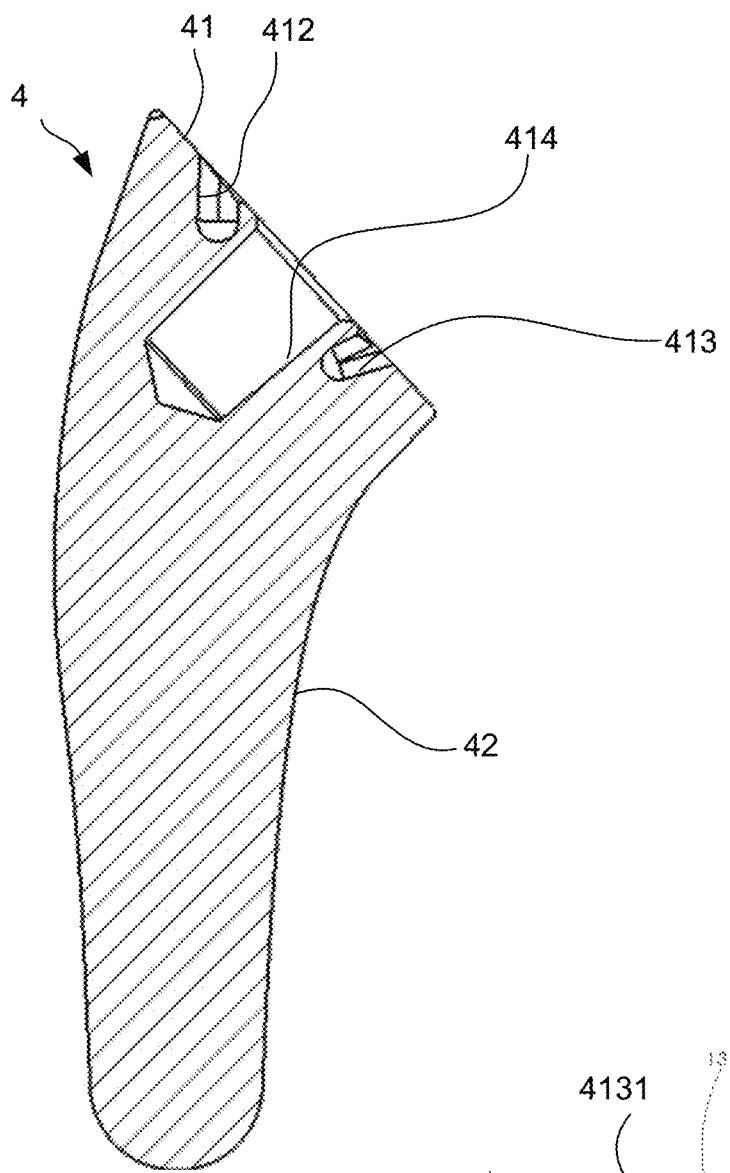
FIG. 18 illustrates a front cross-sectional view of an implant stem, according to embodiments of the present invention.

Inserter 7 includes an impaction head 71 to receive impaction forces from, for example, a mallet. Inserter 7 may further include a handle 72 configured to actuate the gripping and release mechanism for coupling the inserter 7 to the broach 5 and uncoupling the inserter 7 from the broach 5, according to embodiments of the present invention. The inserter 7 may also include a removable depth stop 73. During the broaching process, various sizes of broaches 5 may be coupled with inserter 7 and used to sequentially expand the cavity in bone B, for example from smallest to largest broach 5. During the broaching process, the plate 51 (which is coupled with the inserter 7) is free to rotate about pivot point 511. Once the cavity of desired size is obtained, the broach 5 is inserted into the cavity until an underside of the depth stop 73 contacts the proximal resection surface R, as shown in FIG. 15. As shown in FIG. 16, a screwdriver is inserted into hole 514, through inserter 7, in order to lock the plate 51 to the stem 52 at the angle which is closest to the angle at which the plate 51 extends with respect to the stem 52 when the stem 52 is seated in the cavity and the depth stop 73 abuts the resection surface R, according to embodiments of the present invention. According to some embodiments of the present invention, this angle at which the plate 51 is locked to the stem 52 is the angle at which the plate 51 (or face of the broach 510), resection surface R, and the distal surface of the depth stop 73 are all parallel. The handle 72 may be rotated to release the inserter 7 from the broach 5, leaving the proximal surface 510 of the broach 5 substantially flush with the resection surface R, as shown in FIG. 17. The broach 5 may also be used as a trial implant in order to test positioning and kinematic articular motion with various combinations of trays 3 and/or inserts 2, or trial trays 3 and/or trial inserts 2, according to embodiments of the present invention.

In other words, various broaches 5 of various sizes may be provided in a system or kit along with inserter 7 and corresponding implants. This design of broach 5 allows impaction while in the unlocked configuration. The inserter 7 connects to the broach 5 in a manner that allows full articulation of the plate 51 (which may also be referred to as a "neck") without interference with the bone B. The inserter 7 has a depth stop 73 whose bottom surface is flush with the face 510 of the broach 5. During sequential broaching, the final broach is impacted until the depth stop 73 lays flat on the resection surface R. Since the inserter 7/depth stop 73 is connected to the proximal pivoting neck 51, it will automatically manipulate the proximal portion 51 so that face 510 is substantially coplanar to the resection surface R. A screwdriver can then be reached through the inserter to lock the plate 51 of broach 5 at the particular angle, and the inserter 7 may be removed. The broach 5 now replicates the implant stem at the proper angle, without additional insertion or removal of additional components that could jeopardize the press fit of the final implant stem. The trial head or trial adapter may then be connected to the broach 5, and the entire construct removed from the bone B. The surgeon may compare the index marks 53 with the reference mark 520 (see FIG. 11) of the locked broach 5 in order to determine the proper implant stem with the same inclination angle, and the trial eccentricity may also be read and replicated when selecting and/or creating the final implant. The various angular rotation positions at which the plate 51 may be locked to the stem 52 may correspond to the number of different implant stems offered in the same kit or system, according to embodiments of the present invention. In other words, the plates 51 rotate to selective positions with respect to the stem 52 in order to exactly replicate the inclination angle of a definitive implant. According to alternative embodiments of the present invention, the plate 51 may be locked at a particular angle with respect to the stem 52 prior to insertion if the resection angle is predetermined, such that the broach 5 acts as a rigid monoblock body. In some cases, the angle position of the plate 51 with respect to the stem 52 can be modified after insertion of the broach 5, for example by loosening the set screw and locking the set screw into a different hole.

As discussed above, a shoulder implant involves insertion into and extraction from (during surgery) the humerus with an inserter/handle instrument. This instrument helps in the correct placement of the stem with respect to the patient's natural retroversion of the humerus, and also provides a method of removing the implant stem (and/or broach 5) during surgery. Because the implant stem according to embodiments of the present invention is configured to be substantially flush with a resection surface R of the humerus, there is no collar or other mechanism above the resection surface to provide additional room for gripping by the inserter. Adding additional material to the stem may compromise desired biomechanics.

Figure 19:
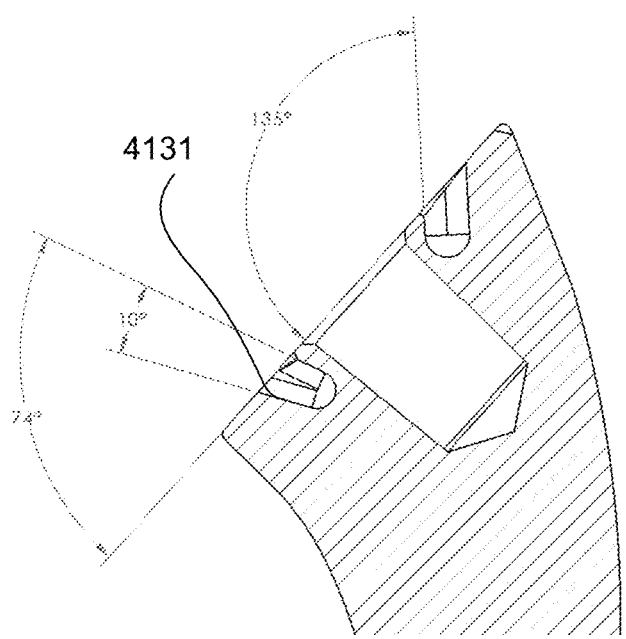
FIG. 19 illustrates a partial back cross-sectional view of the implant stem of FIG. 18, according to embodiments of the present invention.
Figure 20:
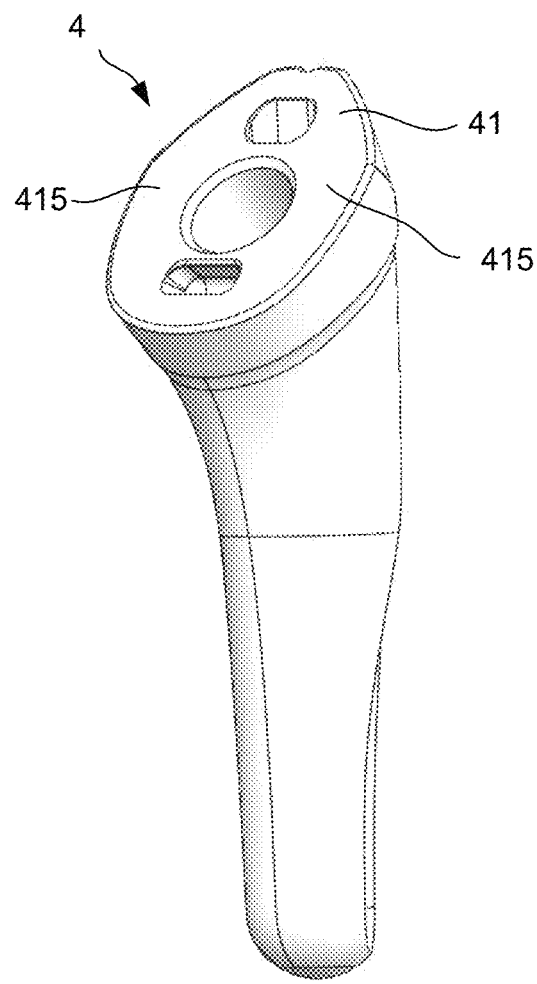
FIG. 20 illustrates a front perspective view of an implant stem, according to embodiments of the present invention.
Figure 21:
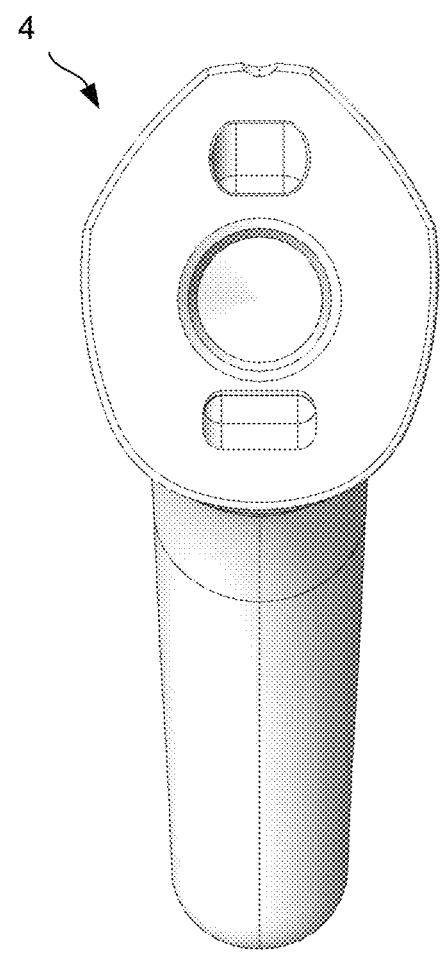
FIG. 21 illustrates a medial elevation view of an implant stem, according to embodiments of the present invention.

FIGS. 18-21 illustrate an implant stem 4, according to embodiments of the present invention. Stem 4 includes a stem portion 42 and two recessed grooves 412, 413 on the proximal face 41 of the implant 4. These grooves 412, 413 provide for attachment to the inserter 7, in a manner similar to the attachment of inserter 7 to grooves 512, 513 of broach 5. For example, the geometry of the grooves 412, 413, including their shape and/or arrangement with respect to the proximal face 41 of stem 4, may be similar to or the same as the geometry of the grooves 512, 513 of the broach 5, including their shape and/or arrangement with respect to the proximal face 510 of the broach 5. These grooves 412, 413 are configured to work on a stem 4 that does not have any material resting above the resection surface R, according to embodiments of the present invention. According to some embodiments of the present invention, no contact is made with the implant taper connection 414, because the taper 414 is often a critical component for locking the assembly of implant components to the stem 4 (e.g. the direct locking of the tray 3, or a convex articulation surface bearing component, to the stem 4, as well as the indirect locking of the inserter 2 to the stem 4 via the tray 3). Impaction forces applied to inserter 7 are directed onto the proximal face 41 of the implant 4 (e.g. at locations 415) and along the medial edge 4131 of the medial groove 413. According to some embodiments of the present invention, the medial groove 413 is tapered at ten degrees (e.g. the medial and lateral walls of the medial groove 413 are tapered ten degrees with respect to each other in a distally-converging manner as shown in FIG. 19) to increase the stability of the implant groove and mating feature of the inserter 7 and guide the location of the impaction force to the top of the groove 413. According to some embodiments of the present invention, the proximal surface 41 itself takes most of the impaction force via direct contact with a distal surface 74 of inserter. Both grooves 412, 413 are angled with respect to the proximal face 41 in order to achieve better gripping and holding power for resisting forces during insertion, impaction, and/or extraction.

Figure 22:
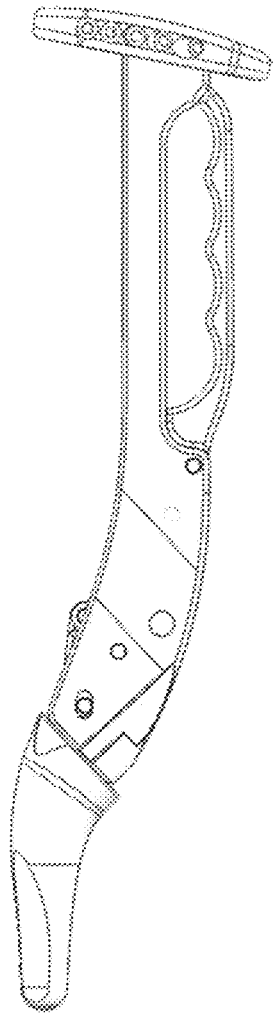
FIG. 22 illustrates a front elevation view of an inserter coupled with an implant stem, according to embodiments of the present invention.
Figure 23:
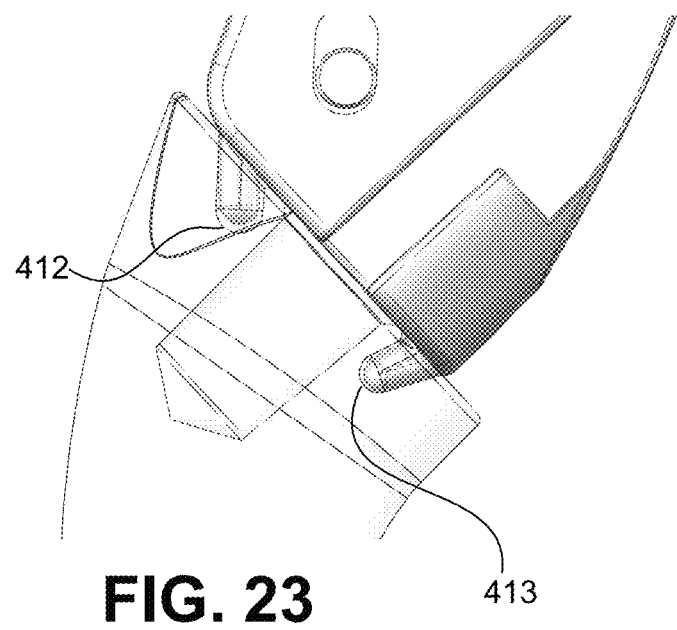
FIG. 23 illustrates a partial front elevation view of the inserter coupled with the implant stem of FIG. 22, with the implant stem shown in phantom, according to embodiments of the present invention.
Figure 24:
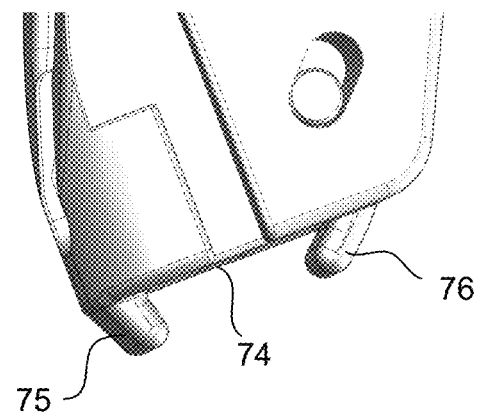
FIG. 24 illustrates a partial back elevation view of an inserter distal end, according to embodiments of the present invention.
Figure 24A:
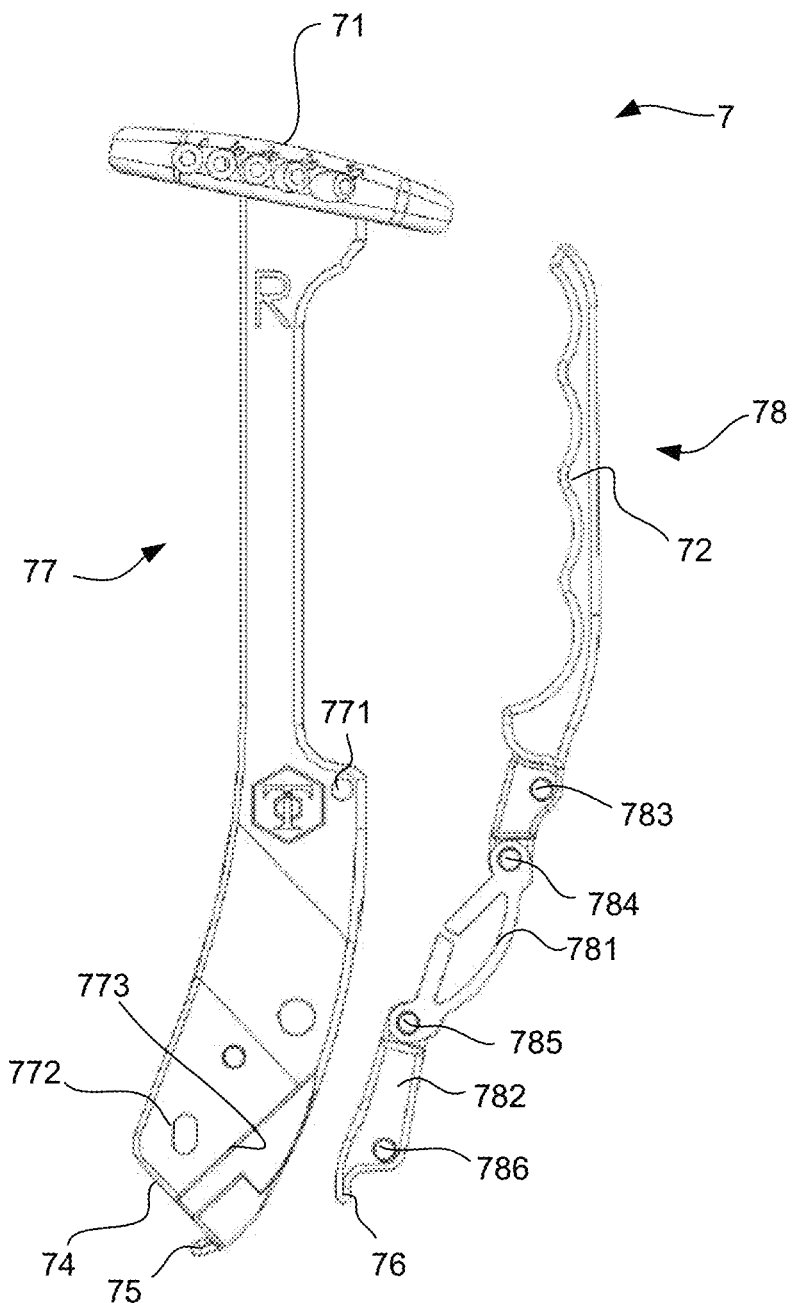
FIG. 24A illustrates a front elevation partially exploded view of a half of a stationary assembly and a movable assembly of an inserter, according to embodiments of the present invention.

As illustrated in FIGS. 22-24, the inserter includes a lateral peg 75 which is fixed with respect to the rest of the inserter 7 and does not move, and also a medial peg 76 which is at least partially extendable and retractable from the distal surface 74 via actuation of the handle 72 of the inserter. The lateral peg 75 may be inserted into lateral groove 412, and the medial peg 75 may be extended from surface 74 into the medial groove 413 in order to solidly grip the implant 4 with the inserter 7. The converging angle of the lateral peg 75 with respect to the medial peg 76 draws the proximal surface 41 against the distal surface 74, which also serves to better distribute impaction forces across a larger surface area of the proximal surface 41, according to embodiments of the present invention.

FIGS. 24A-24D provide additional illustration about the operation of the inserter 7, according to embodiments of the present invention. The inserter 7 includes two assemblies, the stationary assembly 77 and the movable assembly 78. The movable assembly 78 includes a handle 72, a spring link 781, and a peg actuation link 782. The peg actuation link 782 includes the lateral peg 76. The handle 72 is rotatably (e.g. pivotably) coupled to the spring link 781 at pivot 784, and the spring link 781 is rotatably (e.g. pivotably) coupled to the peg actuation link 782 at pivot 785, according to embodiments of the present invention. The stationary assembly 77 includes a pivot location 771 at which the handle 72 pivotably attaches to the stationary assembly 77, such that pivot 784 is at pivot location 771 and handle 72 pivots about stationary assembly 77 at pivot location 771. Pivots 784 and 785 are not coupled to the stationary assembly 77. Pivot 786 includes an axle or rod which is seated within the slot 772 of stationary assembly 77, such that peg actuation link 782 rotates with respect to stationary assembly 77 at pivot 786 and also slides or translates with respect to stationary assembly 77 along slot 772, according to embodiments of the present invention.

Figure 24B:
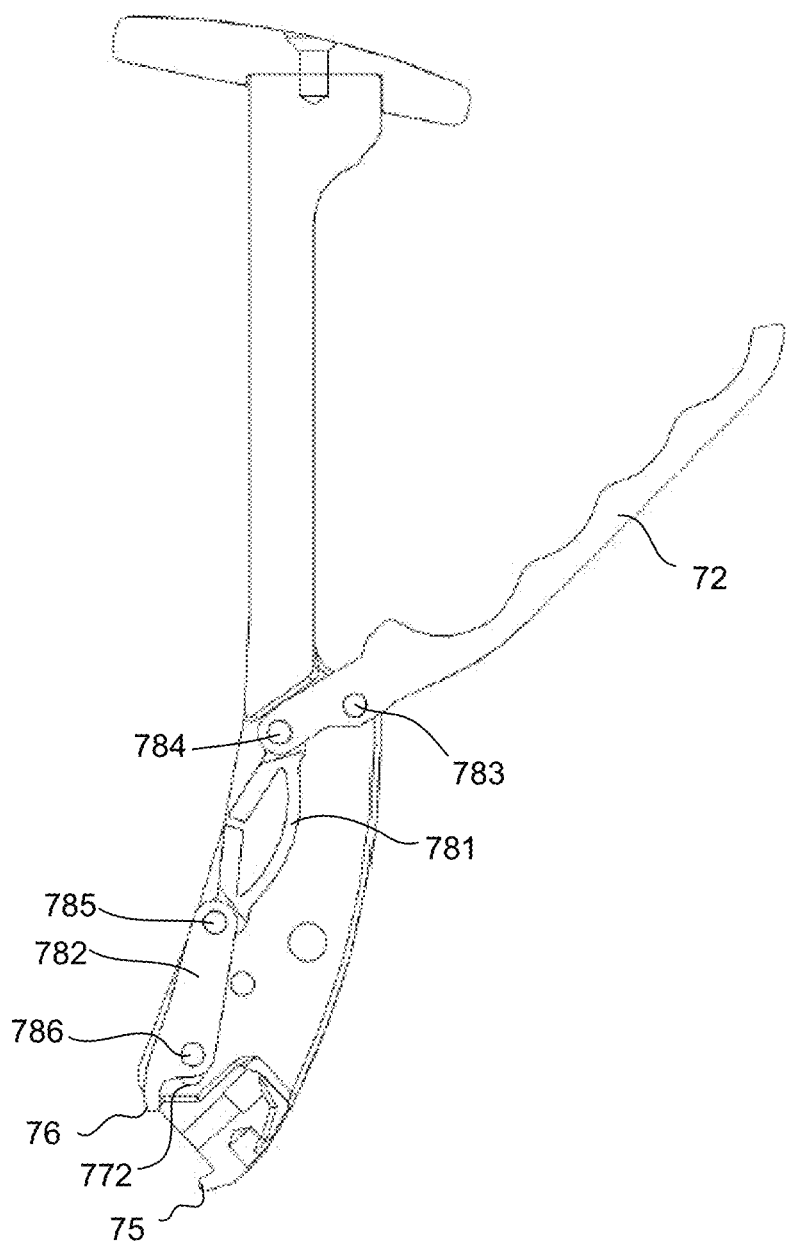
FIG. 24B illustrates a partial cut-away front elevation view of an inserter in an open position, according to embodiments of the present invention.

As shown in FIG. 24B, when handle 72 is in an open position, the peg 76 is retracted or substantially retracted with respect to a distal surface 74 of the inserter 7. In this open position, the peg 786 is situated in a proximal end of the slot 772. When the inserter is in this open position, the surgeon may easily pass the medial peg 75 into the slot 513 on the plate 51 of broach 5 (or into the slot 413 on the stem 4), and may align the lateral peg 76 with the lateral slot 512 on the plate 51 of the broach 5 (or with the lateral slot 412 on the stem 4). While the distal surface 74 of the inserter 7 is kept adjacent to the proximal surface 510 of plate 51 (or the proximal surface 41 of stem 4), the handle 72 may be moved toward the closed position (e.g. back toward the stationary assembly 77). Between the open position of FIG. 24B and the partially closed position of FIG. 24C, the movable assembly 78 advances the peg 76 along a substantially linear path into the slot 512 (or slot 412) as the peg 786 translates from the proximal end of the slot 772 to the distal end of the slot 772. Once the peg 786 reaches the distal end of the slot 772, and the handle 72 is moved toward the closed position shown in FIG. 24D, the motion of the peg actuation link 782 shifts from one of primarily translation to one of primarily rotation, as the proximal end of link 782 (e.g. at pivot 785) moves outwardly in a lateral direction and the link 782 rotates about peg 786 to angle the peg 76 within the slot 512 (or slot 412) closer to the other peg 75, so as to apply a gripping force to the broach 5 (or the implant 4 as the case may be). In the closed position of FIG. 24D, the spring link 781 has been compressed (e.g. the spring gap 7810 has been slightly closed), and provides a spring force which helps to hold the peg 76 closed against the broach 5 (or implant 4) when the handle 72 is in the closed position of FIG. 24D.

FIG. 24D also illustrates the removable connection of the depth stop 73 to the inserter 7, via a set screw 731 which may be selectively advanced to engage with a receptacle in the inserter 7. As described above, the distal surface 732 of the depth stop 73 may be aligned in parallel to the resection surface R in order to help select an angle for the pivoting plate 51 of the broach 5 which, in turn, may be used to select an inclination angle for a stem implant 4, according to embodiments of the present invention.

Often, the humeral head is resected without angle guidance. The trial stems and implants are often set at particular inclination angles. As such, there is often some degree of resection correction that occurs in order to ensure that the resection surface is substantially coplanar with the face of the trial and the implant stem. Additionally, the resection cut may not be adequately flat, and/or may include bony features that would prevent proper assembly of the trial or implant stem with the head or reverse adapter trials or implants. To mitigate this issue, a planer may be used to flatten the resection surface. In order to decrease the risk of impingement with bone B prior to the planer sitting flush on the trial or implant stem face, the planer may be actuated in an elevated position parallel to the trial or implant stem face. The planer may maintain this parallel relationship through the entire reaming process until the planer is flush on the proximal face 41, according to embodiments of the present invention.

Some reamer systems use a cannulated approach in which a post is threaded into a trial stem perpendicular to the implant face and a cannulated planer is engaged with and translates down the post to complete the reaming process. This involves a secondary instrument and two additional surgical steps (insertion and removal of the post). And typically such systems do not permit an ability to thread the post into the definitive implant, and thus permit reaming only with respect to the trial implant.

Figure 25:
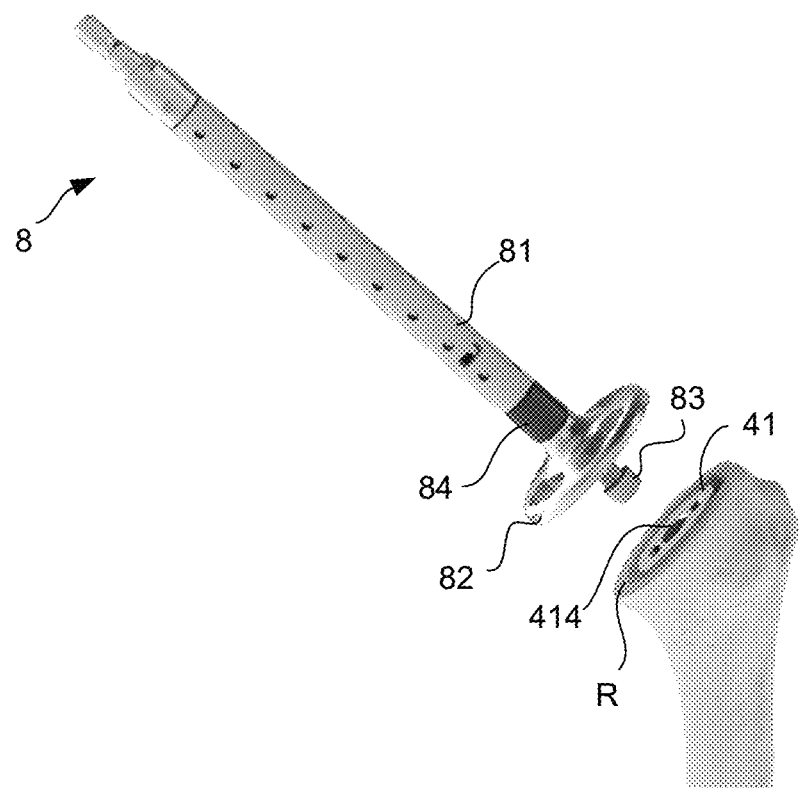
FIG. 25 illustrates a bone reamer device being inserted into a taper hole of an implant stem, according to embodiments of the present invention.
Figure 26:
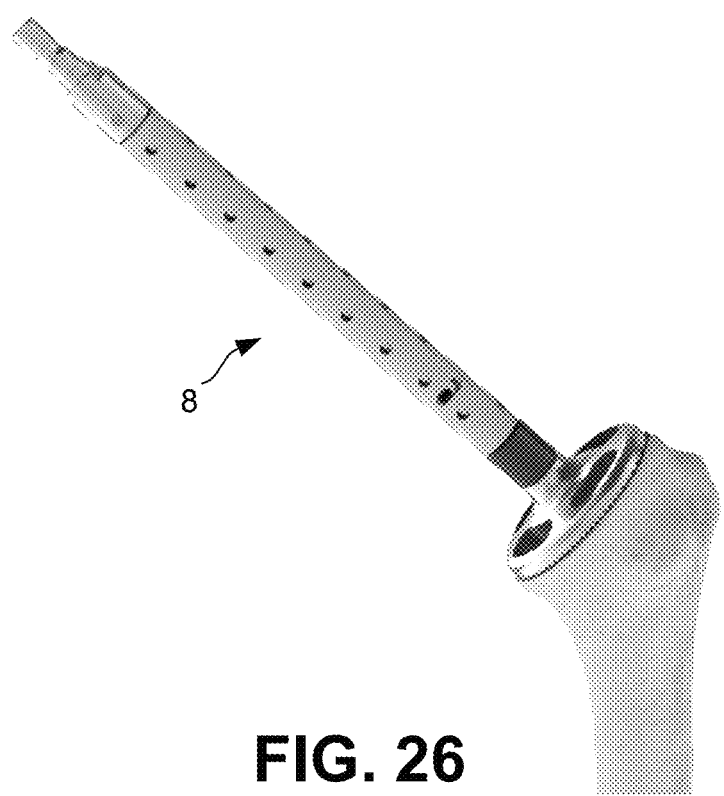
FIG. 26 illustrates the bone reamer device of FIG. 25 reaming bone around the implant stem to form a perpendicular resection surface, according to embodiments of the present invention.

As illustrated in FIGS. 25 and 26, a reamer 8 includes a post 83 that maintains perpendicularity with the trial or implant stem face 41. Post 83 is made of a material that does not damage the taper 414 but which rigidly engages the taper 414. The post 83 moves axially independently of the reamer blade 82, and may be spring loaded. The spring may bias the post 83 toward a normally extended position with respect to the reamer blade 82. This permits the user to engage the taper 414 with the post 83, apply power causing a reaming action of the reaming blade 82, and then depress the reamer 8 (to load the spring) independent of the post 83, to remove any bone that is proud of the trial or implant stem face 41 plane, according to embodiments of the present invention. The reamer 8 may function similarly with respect to a trial stem 5 and an implant stem 4, and can be operated by hand or under power, for example via a Hudson connection. Various diameters of reamer heads 82 may be used to accommodate different resection diameters, according to embodiments of the present invention. A color-coded band 84 may be included on the reamer shaft 81 in order to distinguish it from other reamers or reamer heads 82 of different diameters.

FIGS. 26A and 26B further illustrate the operation of reamer device 8, according to embodiments of the present invention. An inner shaft 85 is coupled to a proximal connector 850 such that manual or motorized rotation of connector 850 rotates shaft 85 within sleeve 81. Shaft 85 is also coupled to reamer blade 82, such that rotation of shaft 85 rotates reamer blade 82. A post shaft 86 is coupled to the shaft 85 such that post shaft 86 translates along a proximal-distal direction (e.g. axially) with respect to shaft 85, but such that shaft 85 rotation is not imparted to post shaft 86. As such, post shaft 86 freely rotates about shaft 85. A spring 860 is situated between shaft 85 and post shaft 86, and operates to bias the post shaft 86 in an extended position with respect to the shaft 85. The post 83 is shaped so as to mate with the hole 414 in the implant 4 such that the central axes of post 83 and post shaft 86 are maintained substantially perpendicular to the proximal face 41 of the implant 4. The post 83 may be threadably engaged with a distal end of the post shaft 86, as illustrated in FIG. 26A. A force in the distal direction to push the shaft 85 and reamer blade 82 downward compresses spring 860 and moves the reamer blade 82 into contact with bone to ream the bone. The post shaft 86 may include a slotted portion 860 along a portion of its axial length, which may interact with a depth stop 851. The slotted portion 860 may be, for example, a portion of the post shaft 86 with a smaller diameter along a certain axial length. The depth stop 851 may be, for example, a ring having an inner diameter that is larger or the same as the outer diameter of the post shaft 86 along the slotted portion 860, but smaller than the outer diameter of the post shaft 86 immediately above and below the slotted portion 860, according to embodiments of the present invention. When the shaft 85 and reamer blade 82 is pushed distally far enough, the distal advancement of the reamer blade 82 with respect to the post 83 will be stopped by the depth stop 851 hitting against the distal end of slotted portion 860.

As an additional or alternative depth stop mechanism, the distal surface of the reamer blade 82 may include a non-cutting portion 821 that may be configured to halt the distal advancement of the reamer blade 82 with respect to the post 83 when the non-cutting portion 821 contacts a proximal surface 41 of the implant stem 4, according to embodiments of the present invention. The non-cutting portion 821 may correspond in diameter to a minimum or maximum dimension of the radial extent of the proximal surface 41 of the implant stem 4 as measured from the central axis 4140 of the hole 414 (see FIG. 28), which prevents the cutting teeth 820 from roughening or damaging the proximal surface 41, according to embodiments of the present invention. The non-cutting portion 821 may, in some embodiments, have an axial depth that is slightly greater than the axial extent of the cutting teeth 820, in order to ensure that the teeth 820 do not contact the implant 4 face 41. The reamer blade 82 may further include discontinuities 822 to permit cut bone to pass from the distal surface to the proximal side of the reamer blade 82, according to embodiments of the present invention.

Varying philosophies exist among surgeons regarding the preferred inclination angle that should be used for a reverse shoulder prosthesis. For various reasons, 145 degrees is believed to be a compromise between high inclination angles that may cause scapular notching and low inclination angles that may result in more limited abduction or range of motion. A shoulder implant system that is capable of achieving a range of angles is optimal. Such a system provides surgeons with options to permit them to utilize their ideal configuration to provide optimum biomechanics, range of motion, and patient outcomes.

Figure 27:
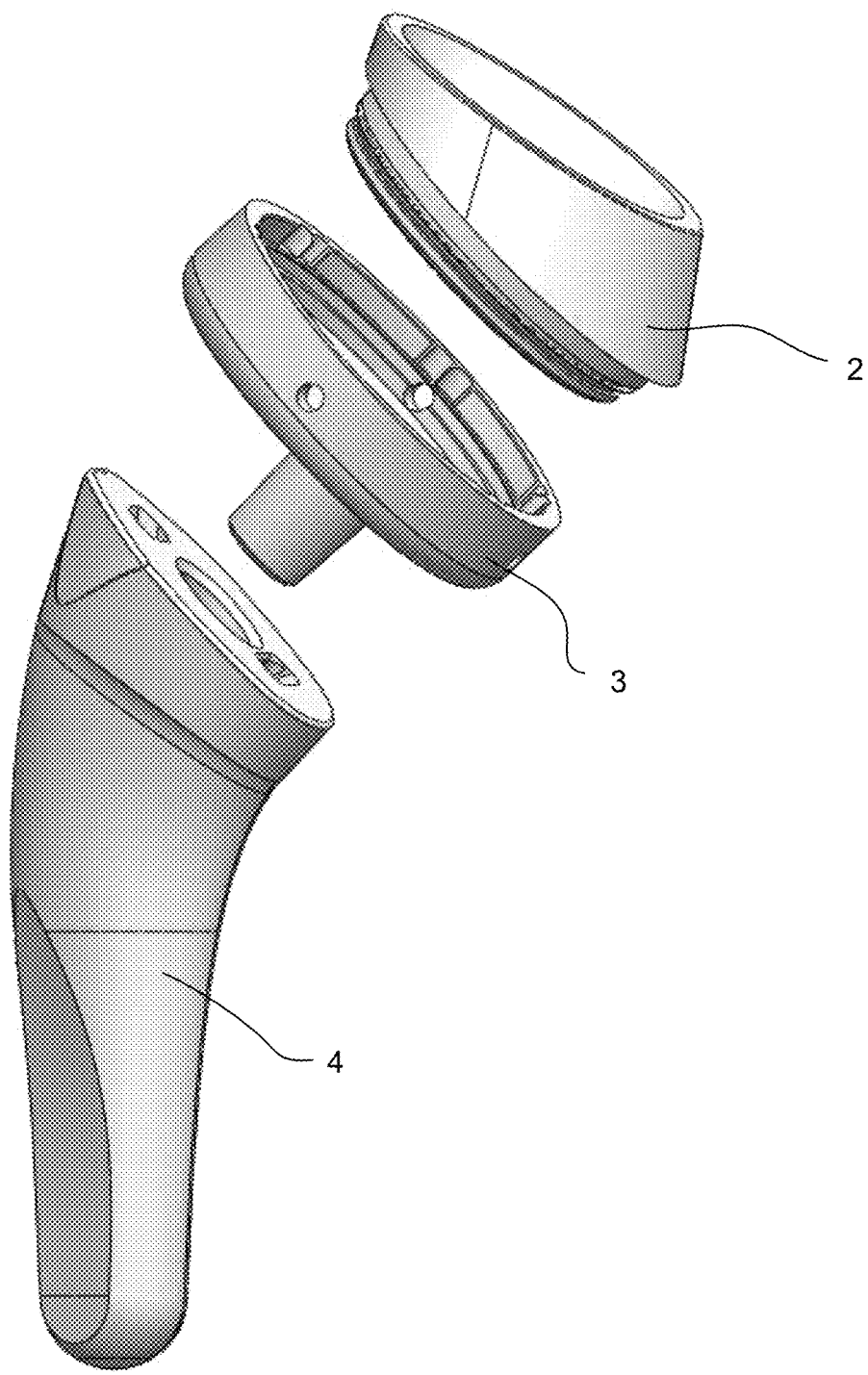
FIG. 27 illustrates a front perspective exploded view of an implant stem, tray, and insert, according to embodiments of the present invention.
Figure 28:
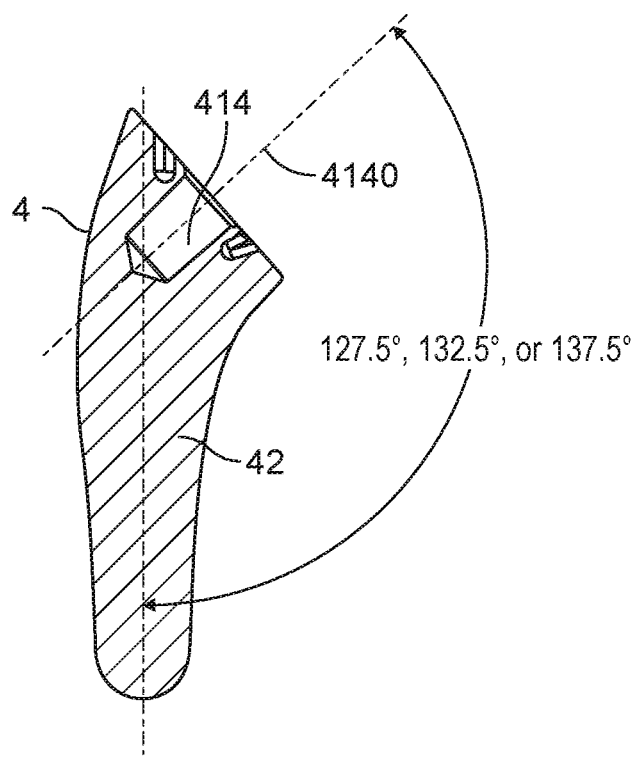
FIG. 28 illustrates a front cross-sectional view of an implant stem, according to embodiments of the present invention.
Figure 31:
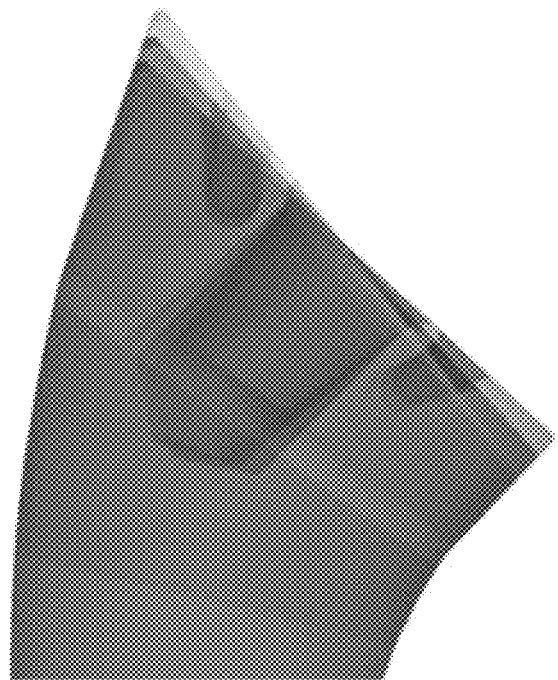
FIG. 31 illustrates three different implant stem angles shown in phantom and superimposed one upon the other, according to embodiments of the present invention.

As shown in FIG. 27, a reversed implant prosthesis according to embodiments of the present invention includes a humeral stem 4, which may be made of metal, a reverse tray 3, which may be made of metal, and a reverse insert 2, which may be made of polymer such as polyethylene. According to some embodiments of the present invention, the humeral stem 4 may be offered in a number of different inclination angles, for example 127.5 degrees, 132.5 degrees, and 137.5 degrees. Stems 4 with additional or different inclination angles may be used. FIG. 31 illustrates stems 4 with three different inclination angles superimposed upon each other. As illustrated in FIG. 28, an inclination angle is measured from a center axis of the stem portion 42 to a center axis of the taper 414. According to some embodiments of the present invention, the center axis of stem portion 42 is a central axis of the distal end of the stem portion 42. According to some embodiments of the present invention, the center axis of the stem portion 42 is the axis which, as an engineering constraint, is selected to coincide with a central axis of a long bone into which the stem 4 is designed to be implanted.

Figure 29:
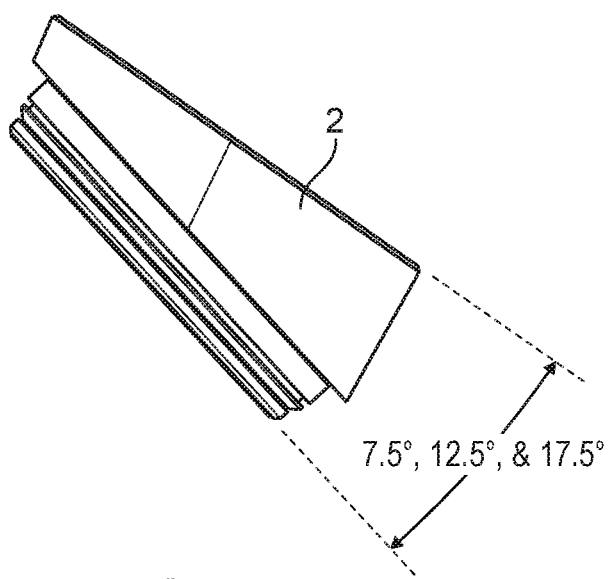
FIG. 29 illustrates a front elevation view of an insert, according to embodiments of the present invention.
Figure 32:
FIG. 32 illustrates a front elevation view of an insert having a 7.5 degree inclination angle, according to embodiments of the present invention.
Figure 33:
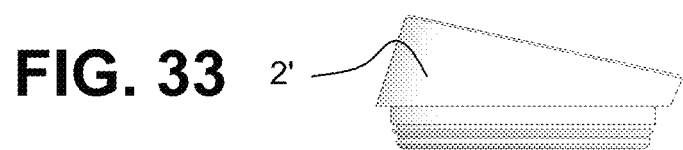
FIG. 33 illustrates a front elevation view an insert having a 12.5 degree inclination angle, according to embodiments of the present invention.
Figure 34:
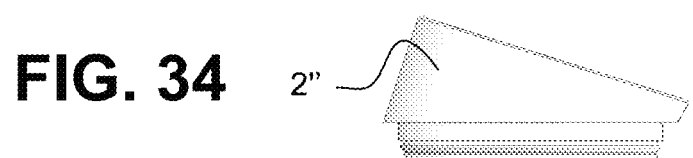
FIG. 34 illustrates a front elevation view of an insert having a 17.5 degree inclination angle, according to embodiments of the present invention.

The reverse insert 2 may be offered in a number of different inclination angles, for example 7.5 degrees, 12.5 degrees, and 17.5 degrees. Inserts 2 with additional or different inclination angles may be used. As shown in FIG. 29, the inclination angle of an insert 2 is measured as the angle between the bottom flat surface and the top flat surface. FIG. 32 illustrates an insert 2 with inclination angle of 7.5 degrees; FIG. 33 shows an insert 2' with an inclination angle of 12.5 degrees; and FIG. 34 illustrates an insert 2'' with an inclination angle of 17.5 degrees.

Figure 30:
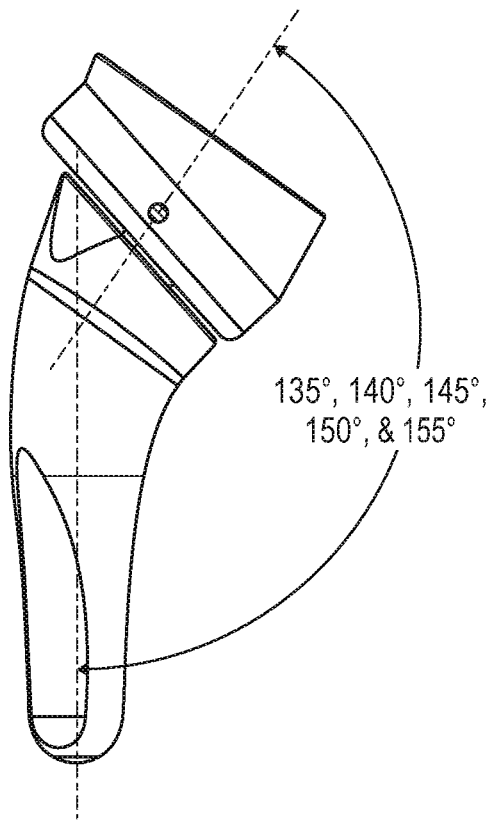
FIG. 30 illustrates a front elevation view of an tray coupled to an implant stem and an insert coupled to the tray, according to embodiments of the present invention.

As shown in FIG. 30, different stem 4 and insert 2 combinations may be coupled together (e.g. via tray 3) to achieve various total implant inclination angles. For example, using the stems 4 with inclination angles of 127.5, 132.5, and 137.5 degrees with inserts of 7.5, 12.5, and 17.5 degrees leads to total possible implant inclination angles of 135, 140, 145, 150, and 155 degrees. FIG. 35 illustrates an implant assembly with a total inclination angle of 135 degrees; FIG. 36 illustrates an implant assembly with a total inclination angle of 145 degrees; and FIG. 37 illustrates an implant assembly with a total inclination angle of 155 degrees. FIG. 38 illustrates the various combinations of stem 4 angles with insert 2 angles to result in various total inclination angles, according to some embodiments of the present invention.

According to embodiments of the present invention, a kit includes at least three stems 4 each having a different inclination angle, at least one tray 3, and at least three inserts 2 each having a different inclination angle. The fact that various inserts 2 can be matched with various stems 4 permits the stem to be placed precisely at the anatomic neck resection to best match the patient's anatomy, while still permitting a desired overall implant inclination angle (e.g. 145 degrees) to be achieved. This is superior to existing reverse prosthesis systems which often have a fixed angle stem that requires humeral resection at the specific angle, which often does not match the native anatomic neck.

Figure 38A:
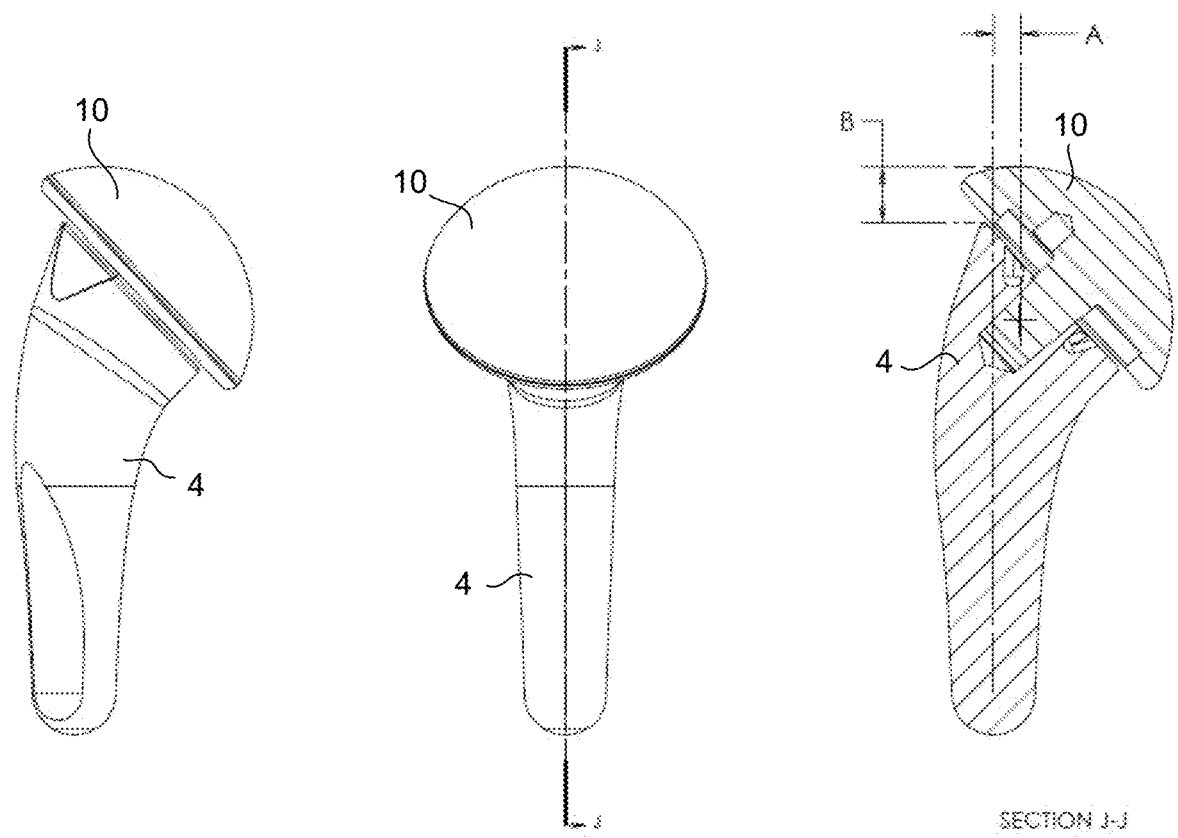
FIG. 38A illustrates an anatomical humeral head implant used with the implant stem of FIGS. 18-21, according to embodiments of the present invention.

During a normal humeral head replacement surgery, one of the stems 4 may be used to anchor the humeral head implant 10. FIG. 38A illustrates a humeral head implant 10 used in an anatomical humeral head replacement and implanted with the same stem 4 that may be later re-used in converting the implant arrangement to a reverse shoulder implant. The distal surface 120 of the implant 10 is configured to abut the proximal surface 41 of the implant stem 4, as shown in FIG. 38A. To fit the normal bony anatomy of the humerus, the stem 4 may be offered in several fixed inclination angles in the range of 125 to 140 degrees. The humeral head 10 for the anatomical implant may be offered according to a range of one or more given thicknesses for a given cut/resection diameter. For example, FIGS. 38B-38D illustrate three different sizes of humeral head implants all having the same stem 11 geometry—FIG. 38B shows an implant 10 with a humeral head portion 12; FIG. 38C shows an implant 10' with a humeral head portion 12' that is larger (e.g. has a larger radius of curvature) than humeral head portion 12; and FIG. 38D shows an implant 10'' with a humeral head portion 12'' that is larger (e.g. has a larger radius of curvature) than humeral head portion 12'. The different sizes of implants 10, 10', and 10'' permit the surgeon to tune the implant to the soft tissue tension in the joint; each head 12, 12', 12'' is offered at different thicknesses/radii of curvature. A thicker head 12'' puts more tension on the soft tissue of the joint, while a thinner head 12 puts less tension on the soft tissue of the joint. The bottom surface 120 of the implants 12 are configured to be coplanar with the face 41 of the stem 4. The assembly of the humeral head to the stem 4 may be achieved via a well-known Morse taper 11 forming a male protuberance on the humeral head and a female recess 414 into the stem.

A multiplicity of humeral heads may be provided, and each may include a different position of the male protuberance for engaging the taper recess 414. FIG. 38E shows one example of an implant 10''' having an angle SA formed between the central axis 101 of the stem 11' and the central axis 111 of the humeral head portion 12, according to embodiments of the present invention. The implant 10''' shown in FIG. 38E includes an angle SA of ten degrees. Anatomical shoulder implant systems according to embodiments of the present invention may include various implants 10''' having varying angles SA. For example, an anatomical shoulder implant kit may include implants 10''' having angles SA which pair with the inclination angles of the stems 4 offered, in order to permit the surgeon to pair a particular anatomical implant 10''' with a stem 4 having a particular inclination angle to achieve a final anatomical inclination angle that is consistent with commonly targeted final inclination angles in anatomical shoulder replacement, similar to how the inserts 2 may be paired with the same stems 4 in the manner described below for reverse shoulder implants, according to embodiments of the present invention.

Figure 39:
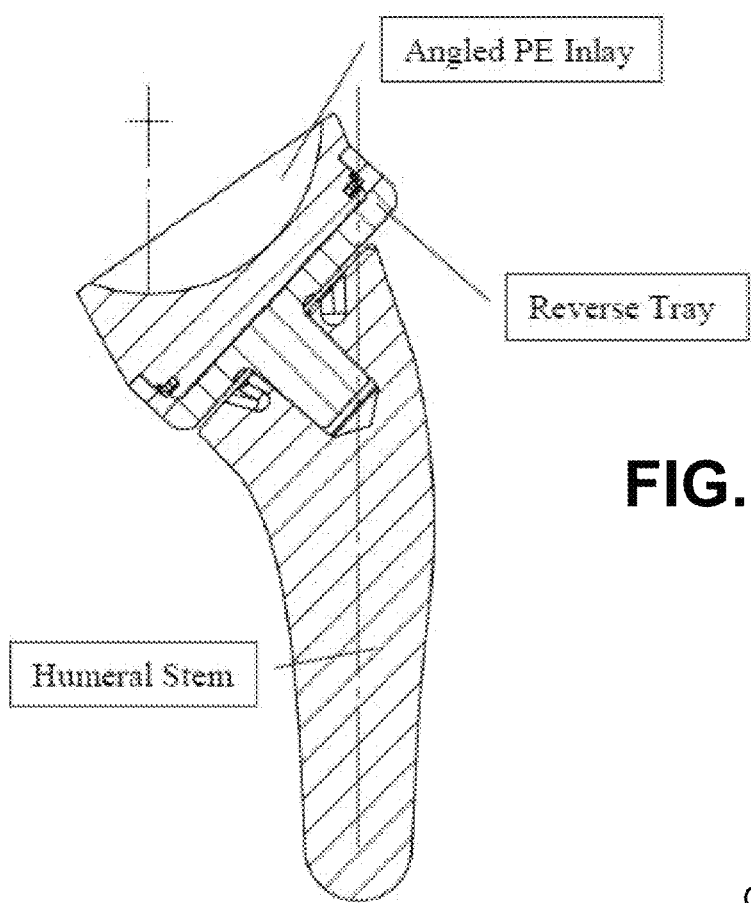
FIG. 39 illustrates a front cross-sectional view of an implant stem, tray, and insert, according to embodiments of the present invention.
Figure 40:
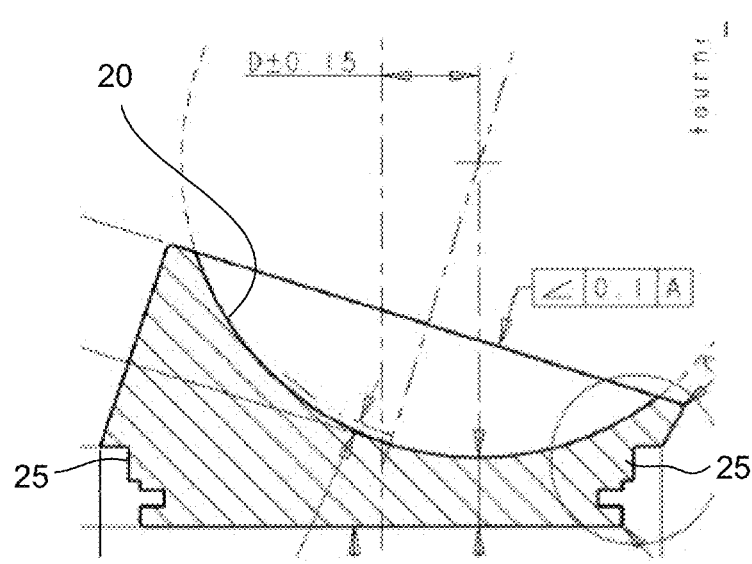
FIG. 40 illustrates a cross-sectional view of an insert, according to embodiments of the present invention.
Figure 41:
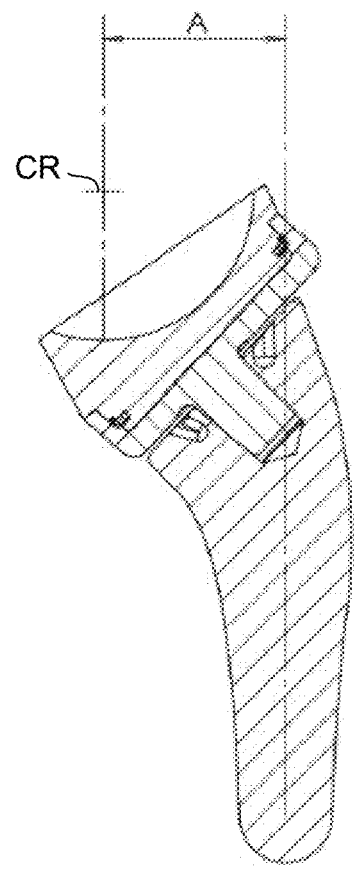
FIG. 41 illustrates another front cross-sectional view of an implant stem, tray, and insert, according to embodiments of the present invention.

In a reverse reconstruction of such a humeral head implant, the implant kit may include a reverse tray 3 of a given diameter featuring the same male taper/protuberance that was previously used with the humeral head implant, as well as at least one insert 2 of a diameter corresponding or paired to that of the tray 3 and designed to mate with the reverse tray, for example in the manners described above. This is illustrated in FIG. 39, for example. The insert 2 may be angled accordingly to the stem 4 inclination angle such that the final implant inclination angle is in the range of 110 to 155 degrees, according to embodiments of the present invention. As shown in FIG. 40, the center of the radius of curvature or center of rotation of the recess 20 in the insert 2 is not aligned with the axis of the cylindrical sidewall 25, but is instead slightly offset toward a thinner portion of the insert 2. As shown in FIG. 41, a distance between the center of rotation CR (e.g. the origin or center of the radius of curvature or rotation of surface 20) and the stem 4 axis may be between 22 and 28 millimeters, depending on the stem size and inclination angle, according to embodiments of the present invention.

A stem 4 according to embodiments of the present invention may be collarless, may be offered with various inclination angles (e.g. 127.5, 132.5, and 137.5 degrees), and may include a distance between the entry point of the taper 414 and the longitudinal axis of the stem 4. A reverse tray 3 according to embodiments of the present invention may include an outer diameter of, for example, 40 millimeters. The tray 3 may be formed without a skirt, so as to mate with the collarless stem 4 design and to reduce the combination of stack-up or overall height. Although tray 3 is shown without a skirt, tray 3 may alternatively include a skirt in some embodiments. The thickness of the tray 3 between the bottom inside surface 36 and bottom outside surface 38 (see FIG. 5) may be between three millimeters (e.g. the minimal thickness to avoid breakage of the tray 3) and four millimeters (e.g. to avoid over-tension of the tray 3), according to embodiments of the present invention. This component may alternatively have other thicknesses. In order to minimize the risk of breakage of the male taper 391, a circular recess 39 is formed on the lower surface 38 of the tray 3 at the base of the taper 391, according to embodiments of the present invention. The recess 39 may be between 0.5 to 1.0 millimeters deep (depending on the thickness of the tray 3), and the cross-sectional shape of the recess 39 may be a semi-circle with a diameter of three millimeters. Various alternative trays 3 may be offered; for example, one tray 3 may have a taper 391 whose taper axis is aligned with a central axis of the tray 3, while another tray 3 may have a taper 391 that is offset from the central axis of the tray 3, according to embodiments of the present invention. Tray 3 may also be offered in a low offset variation in which the taper 391 axis is offset by about 1.5 millimeters with respect to the tray 3 axis, and in a high offset variation in which the taper 391 axis is offset by about 3.5 millimeters with respect to the tray 3 axis.

As described above, the insert 2 may be offered in various angles, for example 17.5, 12.5, and 7.5 degrees to interact with the angle of the stem 4 and to provide a desired final implant inclination angle (e.g. 145 degrees). According to some embodiments of the present invention, the center or origin of the radius of curvature or rotation of the concave articular surface 20 is offset from the axis of the engagement cylinder 25 by five to eight millimeters, in an offset direction toward the thinnest portion of the insert 2. As described above, the insert 2 cooperates and engages with the tray 3 at any angular position of the insert 2 with respect to the tray 3.

Embodiments of the present invention include stems 4 having a taper entry point 414 that is eight to eleven millimeters offset from the stem longitudinal axis, a reverse tray 3 with a male taper 391 being infinitely dialable at any angular position with respect to the stem 4, an angled insert 2 having superior and inferior faces that form a given angle, with the superior face including an articular recess of which the center of rotation is offset, from the revolution axis of the engagement cylinder 25, towards the thinner portion of the insert 2. The engagement cylinder 25 of such insert 2 may be configured to engage with and cooperate with the tray 3 at any angular position of the insert 2 with respect to the tray 3, according to embodiments of the present invention.

When a humeral head is resected and a trial stem is implanted, the cut surface of the humeral head may beneficially be protected from retractors and other instruments while the surgeon prepares the glenoid side of the joint. A circular plate may be rigidly attached to the trial stem to accomplish this purpose. Typical eccentric cut protectors connect to the trial stem via a screwdriver driving a captured screw. An additional instrument must often be used to connect to the cut protector to dial the eccentricity (e.g. to select the rotational position of the cut protector about its eccentric stem) and hold the cut protector in place while the screw is engaged with the screwdriver. This often requires both hands, multiple surgical steps, and multiple instruments.

Figure 42:
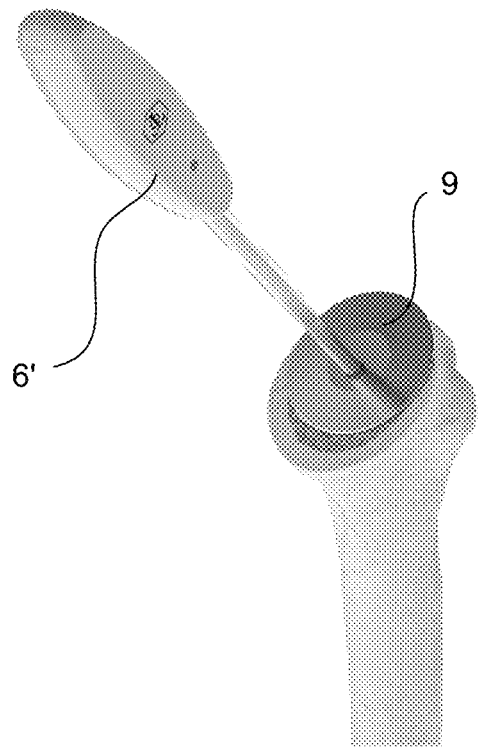
FIG. 42 illustrates a front perspective view of a driver tool used to rotate a cover element, according to embodiments of the present invention.
Figure 43:
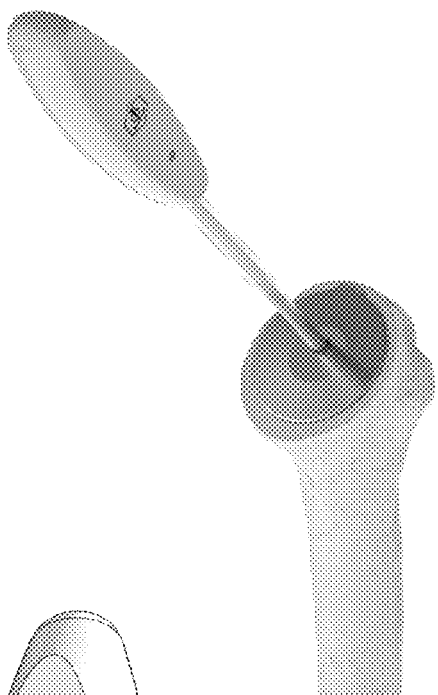
FIG. 43 illustrates a front perspective view of a driver tool used to rotate a cover element, with the cover element in the desired position, according to embodiments of the present invention.
Figure 44:
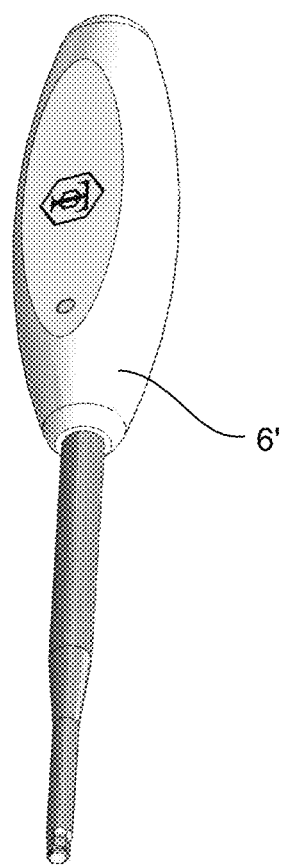
FIG. 44 illustrates a front perspective view of the driver tool of FIGS. 42 and 43, according to embodiments of the present invention.
Figure 45:
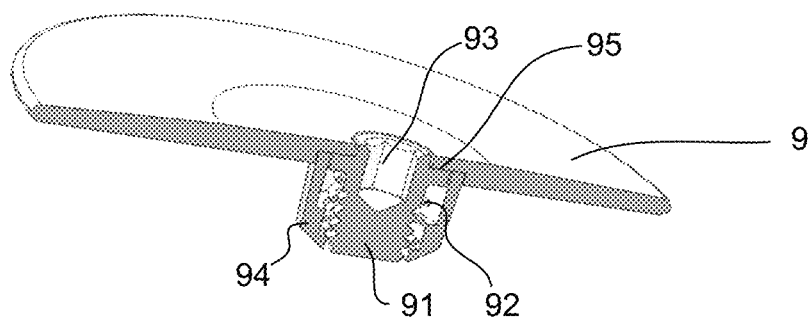
FIG. 45 illustrates a cross-sectional perspective view of the cover element of FIGS. 42 and 43, according to embodiments of the present invention.
Figure 46:
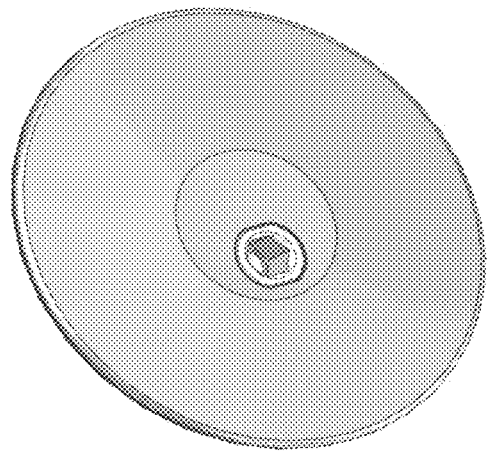
FIG. 46 illustrates a top perspective view of the cover element of FIGS. 42, 43, and 45, according to embodiments of the present invention.
Figure 47:
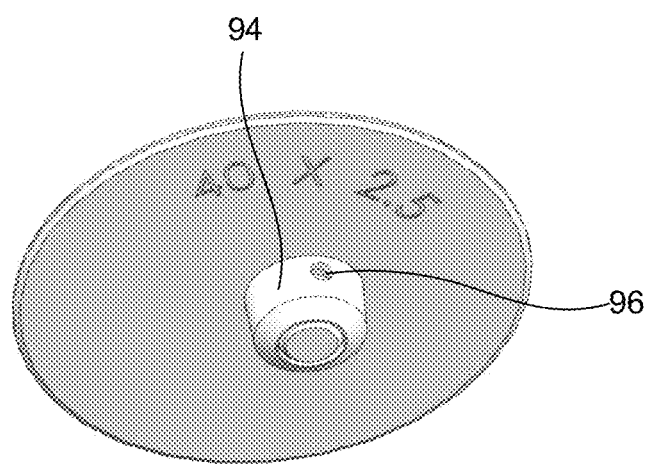
FIG. 47 illustrates a bottom perspective view of the cover element of FIGS. 42, 43, 45, and 46, according to embodiments of the present invention.

As shown in FIGS. 42-47, a cut protector 9, which may also be referred to as a cover element 9, is eccentric, such that it has a boss 94 that is offset from a central axis of the cut protector 9. Due to this eccentricity, the cut protector 9 is rotated to the proper location for maximum or optimal or desired resection coverage, then secured to the trial stem with a captured screw 91. The captured screw 91 includes a driver interface recess 93 configured to mate with the correspondingly-shaped distal end of the driver tool 6'. The driver tool 6' may include a clip that provides friction and retains the screw, and thus the entire cut protector 9, to the end of the driver tool 6'. FIGS. 42 and 43 illustrate a front perspective view of a driver tool used to rotate a cover element, according to embodiments of the present invention. The screw 91 includes a keyed proximal portion that mates with a keyed portion of the cut protector 9. The screw is spring loaded (e.g. by spring 92) to maintain this relationship, such that the screw 91 and the cut protector 9 rotate together.

When the driver tool 6' is rotated, the screw 91 and cut protector 9 also rotate. Thus, the surgeon can be handed the cut protector 9 loaded onto the end (e.g. the hex end) of the driver tool 6'. The surgeon may then mate the boss 94 on the bottom of the cut protector 9 with the cavity 414 in the trial stem, and rotate the driver tool 6' handle so that the cut protector 9 is at a proper orientation for maximum or desired resection coverage.

When proper orientation is achieved, the driver tool 6' may be depressed, which pushes down on the spring-loaded screw 91. The proximal end of the screw 91 becomes disengaged from the keyed feature in the cut protector 9, and the threaded distal end of the screw 91 contacts the mating female threads inside the trial stem. The screw may then be rotated to rigidly connect the two components (the cut protector 9 and trial stem), while the eccentricity of the cut protector 9 is maintained, according to embodiments of the present invention. The screwdriver may then be disengaged. A hole 96 in the boss 94 may facilitate cleaning of the cut protector 9.

Various components or features or processes described herein may be used independently, and/or used in combination with one or more of the other components or features or processes described herein, in all possible combinations. Also, some or all of the components or features or processes described herein may optionally be used in combination with components or processes or features described in PCT Patent Application PCT/EP2012/071618, filed on Oct. 31, 2012 and published on May 10, 2013 as WO 2013/064569, which is incorporated by reference herein in its entirety for all purposes.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for a modular reverse shoulder prosthesis, the system comprising:

a humeral component having a proximal cavity, the proximal cavity including an inner sidewall;

an insert having a distal end and a proximal end, the distal end configured to engage the proximal cavity of the humeral component, the distal end of the insert including an outer sidewall, the outer sidewall formed about an insert axis, the proximal end including a concave articular surface; and fins projecting directly inwardly from the inner sidewall of the proximal cavity, the fins projecting to an inner diameter that is smaller than the outer diameter of the outer sidewall, the fins arranged with respect to the proximal cavity of the humeral component such that the fins secure the insert against rotation about the insert axis with respect to the humeral component by deforming the outer sidewall of the insert.

2. The system of claim 1, wherein the fins are configured to secure the insert against rotation about the insert axis regardless of a rotational position of the insert about the insert axis when the insert is inserted into the humeral component.

3. The system of claim 1, wherein the outer sidewall is at least partially cylindrical and has the outer diameter formed about the insert axis.

4. The system of claim 3, wherein the fins are at least three fins arranged on the inner sidewall in a rotationally symmetrical manner about the insert axis.

5. The system of claim 4, wherein the at least three fins are at least six fins arranged on the inner sidewall in the rotationally symmetrical manner about the insert axis.

6. The system of claim 1, wherein the fins deform the insert by cutting the insert when the insert is inserted into the humeral component.

7. The system of claim 1, wherein the fins deform the insert by inelastically deforming the insert when the insert is inserted into the humeral component.

8. The system of claim 1, wherein a first material out of which the fins are made is harder than a second material out of which the distal end of the insert is made.

9. The system of claim 1, wherein the distal taper is formed about a taper axis, and wherein the taper axis is offset from the insert axis when the insert is inserted into the humeral component, so as to permit eccentric rotation of the humeral component about the taper axis when the distal taper is inserted into the proximal taper of the stem.

10. The system of claim 1, wherein the fins project inwardly from a bottom of the proximal cavity.

11. The system of claim 1, wherein the insert includes a first channel formed circumferentially about the distal end, wherein the insert further includes a snap-fit ring seated at least partially within the first channel, and wherein the humeral component includes a second channel formed circumferentially within the proximal cavity, wherein the snap-fit ring is configured to become seated in both the first and second channels when the insert is inserted into the humeral component so as to secure the insert against separation from the humeral component.

12. The system of claim 11, wherein the snap-fit ring has an at-rest configuration in which an inner diameter of the snap-fit ring is within the first channel and an outer diameter of the snap-fit ring is outside of the first channel, a compressed configuration in which the outer diameter of the snap-fit ring is seated fully within the first channel, and a partially compressed configuration in which the outer diameter of the snap-fit ring is smaller than the outer diameter of the snap-fit ring in the compressed configuration but not entirely seated within the first channel; wherein the snap-fit ring is configured to be in the at-rest configuration prior to insertion of the insert into the humeral component, wherein the snap-fit ring is configured to be in the compressed configuration as the insert is initially inserted into the humeral component, and wherein the snap-fit ring is configured to assume the partially compressed configuration when the snap-fit ring is seated in both the first and second channels.

13. The system of claim 11, wherein the snap-fit ring is configured to compress radially so as to be fully received within the first channel when the insert is first inserted into the humeral component.

14. The system of claim 11, wherein the snap-fit ring includes a discontinuity to facilitate radial compression of the snap-fit ring when the insert is first inserted into the humeral component.

15. The system of claim 14, wherein the snap-fit ring reversibly secures the insert against separation from the humeral component.

16. The system of claim 15, wherein the humeral component includes one or more holes formed from an outer surface of the humeral component to within the second channel of the proximal cavity, wherein the one or more holes permit insertion of a tool to compress the snap-fit ring into the first channel so as to permit release of the insert from the humeral component.

17. The system of claim 11, wherein the snap-fit ring is configured to compress radially, wherein the snap-fit ring includes a distal edge that is chamfered to facilitate compression of the snap-fit ring when the insert is inserted into the humeral component.

18. The system of claim 17, wherein the humeral component includes a chamfered proximal edge configured to interact with the chamfered distal edge of the snap-fit ring.

19. The system of claim 1, wherein the humeral component comprises a distal taper configured to mate with a proximal taper of a stem.

20. The system of claim 1, wherein the fins deform the insert when the insert is inserted into the humeral component.

21. The system of claim 1, wherein the humeral component is configured to mate with a stem.

* * * * *